(12) United States Patent
Katoh et al.

(10) Patent No.: US 7,985,204 B2
(45) Date of Patent: Jul. 26, 2011

(54) REAGENT INJECTION DEVICE

(75) Inventors: Osamu Katoh, Toyohashi (JP); Manabu Shimogami, Nagoya (JP); Atsushi Kureha, Nagoya (JP)

(73) Assignees: Asahi Intecc Co., Ltd., Nagoya-shi, Aichi (JP); Osamu Katoh, Nagoya-shi, Aichi (JP)

( * ) Notice: Subject to any disclaimer, the term of this patent is extended or adjusted under 35 U.S.C. 154(b) by 1084 days.

(21) Appl. No.: 11/575,748

(22) PCT Filed: Jun. 24, 2005

(86) PCT No.: PCT/IB2005/002787
§ 371 (c)(1),
(2), (4) Date: Jun. 6, 2007

(87) PCT Pub. No.: WO2006/043133
PCT Pub. Date: Apr. 27, 2006

(65) Prior Publication Data
US 2007/0299404 A1   Dec. 27, 2007

(30) Foreign Application Priority Data
Oct. 19, 2004   (JP) ................................ 2004-304822

(51) Int. Cl.
*A61M 5/178*   (2006.01)
(52) U.S. Cl. ............................ 604/164.01; 604/164.13
(58) Field of Classification Search .................. 600/114, 600/115; 604/164.01, 164.02, 164.06, 164.07, 604/164.09, 164.1, 164.11, 164.13, 165.01, 604/264, 272
See application file for complete search history.

(56) References Cited

U.S. PATENT DOCUMENTS
RE31,873 E   4/1985   Howes
(Continued)

FOREIGN PATENT DOCUMENTS
EP   1 070 513 A1   1/2001
(Continued)

OTHER PUBLICATIONS

Satoshi Taketani, "New Development of Cardiac Muscle Regeneration Therapy and Cardiac Failure Therapy," slides used at the Far Side Session held on Jun. 30, 2004 as a part of the 13th Annual Meeting of the Japanese Society of Interventional Cardiology, Jul. 1-3, 2004, with partially translated copies.

(Continued)

*Primary Examiner* — Theodore J Stigell
*Assistant Examiner* — Catherine N Witczak
(74) *Attorney, Agent, or Firm* — Knobbe, Martens, Olson & Bear, LLP

(57) ABSTRACT

A needle-like tubular body (12) with its tip formed as a needle, a first guide wire (14), and a second guide wire (16) are inserted into a main tube (10). A first opening and a second opening (28 and 36) through which a first guide wire and a second guide wire (14 and 16) are respectively extended out of the main tube (10) are provided in the main tube (10). A projection aperture (32) through which the needle of the needle-like tubular body (12) is projected out of the main tube (10) is provided in the main tube (10). A support tube (60) that supports the part of the second guide wire (16) extending from the second opening (36) is further provided in the main tube (10).

4 Claims, 18 Drawing Sheets

U.S. PATENT DOCUMENTS

| | | | |
|---|---|---|---|
| 4,578,061 | A | 3/1986 | Lemelson |
| 4,769,005 | A | 9/1988 | Ginsburg et al. |
| 4,808,156 | A | 2/1989 | Dean |
| 5,059,177 | A | 10/1991 | Towne et al. |
| 5,190,528 | A | 3/1993 | Fonger et al. |
| 5,261,889 | A | 11/1993 | Laine et al. |
| 5,263,932 | A | 11/1993 | Jang |
| 5,279,546 | A * | 1/1994 | Mische et al. .................. 604/22 |
| 5,354,279 | A | 10/1994 | Höfling |
| 5,413,581 | A | 5/1995 | Goy |
| 5,419,777 | A | 5/1995 | Höfling |
| 5,464,395 | A | 11/1995 | Faxon et al. |
| 5,702,384 | A | 12/1997 | Umeyama et al. |
| 5,797,869 | A | 8/1998 | Martin et al. |
| 5,906,594 | A | 5/1999 | Scarfone et al. |
| 5,916,194 | A | 6/1999 | Jacobsen et al. |
| 5,921,971 | A | 7/1999 | Agro et al. |
| 6,045,557 | A | 4/2000 | White et al. |
| 6,068,610 | A | 5/2000 | Ellis et al. |
| 6,068,638 | A | 5/2000 | Makower |
| 6,099,497 | A | 8/2000 | Adams et al. |
| 6,135,976 | A | 10/2000 | Tachibana et al. |
| 6,165,195 | A | 12/2000 | Wilson et al. |
| 6,217,554 | B1 | 4/2001 | Green |
| 6,248,122 | B1 | 6/2001 | Klumb et al. |
| 6,283,947 | B1 | 9/2001 | Mirzaee |
| 6,302,870 | B1 | 10/2001 | Jacobsen et al. |
| 6,375,615 | B1 | 4/2002 | Flaherty et al. |
| 6,440,161 | B1 | 8/2002 | Madrid et al. |
| 6,458,098 | B1 | 10/2002 | Kanesaka |
| 6,461,296 | B1 | 10/2002 | Desai |
| 6,544,230 | B1 | 4/2003 | Flaherty et al. |
| 6,547,767 | B1 | 4/2003 | Moein |
| 6,682,536 | B2 | 1/2004 | Vardi et al. |
| 6,682,556 | B1 | 1/2004 | Ischinger |
| 6,689,099 | B2 | 2/2004 | Mirzaee |
| 6,692,466 | B1 | 2/2004 | Chow et al. |
| 6,706,017 | B1 | 3/2004 | Dulguerov |
| 6,884,258 | B2 | 4/2005 | Vardi et al. |
| 6,926,692 | B2 | 8/2005 | Katoh et al. |
| 2001/0011180 | A1 | 8/2001 | Fitzmaurice et al. |
| 2002/0055733 | A1 | 5/2002 | Wilson |
| 2002/0072706 | A1 | 6/2002 | Hiblar et al. |
| 2003/0040712 | A1 | 2/2003 | Ray et al. |
| 2003/0171714 | A1 | 9/2003 | Katoh et al. |
| 2004/0064128 | A1 | 4/2004 | Raijman et al. |
| 2004/0073108 | A1 | 4/2004 | Saeed et al. |
| 2004/0102719 | A1 | 5/2004 | Keith et al. |
| 2004/0106866 | A1 | 6/2004 | Ookubo et al. |
| 2004/0176726 | A1 | 9/2004 | Osamu et al. |
| 2004/0220473 | A1 | 11/2004 | Lualdi |
| 2005/0004522 | A1 | 1/2005 | Katoh et al. |
| 2005/0070874 | A1 | 3/2005 | Masuda et al. |
| 2006/0025720 | A1 | 2/2006 | Sawa et al. |
| 2006/0184156 | A1 | 8/2006 | Jang |

FOREIGN PATENT DOCUMENTS

| | | |
|---|---|---|
| JP | 06-014997 | 1/1994 |
| JP | 08-317988 | 12/1996 |
| JP | 11-057019 | 3/1999 |
| JP | 2001-104487 | 4/2001 |
| JP | 2001-299927 | 10/2001 |
| JP | 2001-299927 A | 10/2001 |
| JP | 2001-314514 | 11/2001 |
| JP | 2002-306606 | 10/2002 |
| JP | 2003-250899 A | 9/2003 |
| JP | 2003-339874 | 12/2003 |
| JP | 2004-267333 A | 9/2004 |
| JP | 2004-528877 A | 9/2004 |
| WO | WO 92/10142 | 6/1992 |
| WO | WO 2006/043133 A2 | 4/2006 |

OTHER PUBLICATIONS

A poster used in a booth of Asahi Intecc Co., Ltd. at The 13$^{th}$ Annual Meeting of the Japanese Society of Interventional Cardiology, Jul. 1-3, 2004.

Etsuo Tsuchikane, "Percutaneous Cell Injection Device to the Myocardium," slides used at CCT2005 in Kobe, Sep. 27, 2005.

* cited by examiner

REAGENT INJECTION DEVICE

This application is the U.S. National Phase under 35 U.S.C. §371 of International Application PCT/IB2005/002787, filed Jun. 24, 2005, which claims priority to Japanese Patent Application No. 2004-304822, filed on Oct. 19, 2004. The International Application was published under PCT Article 21 (2) in a language other than English.

TECHNICAL FIELD

This invention relates to a structure of a reagent injection device that injects a specified reagent into a lesion or other area of a target body tissue.

BACKGROUND ART

Various therapies, examinations, procedures and other processes have conventionally been performed in which a medical apparatus, such as a catheter, is inserted into a variety of human tubular organs and body tissues such as blood vessels, the gastrointestinal tract, the urinary tract, and so on. Recently, therapies and other procedures in which a specified reagent is injected into a lesion in body tissue using a reagent injection device, such as a reagent injection catheter, are also being carried out (e.g., Japanese Patent Laid-open No. 2001-299927).

These reagent injection devices used to inject reagents into lesions, etc., have a structure in which a needle-like tubular body is movably inserted into a main tube. Also, the needle-like tubular body generally has a sharp needle at its tip. Additionally, the tubular body has an inner hole through which a specified reagent is passed. In a reagent injection device having this structure, the needle of the needle-like tubular body projects out of the main tube that has been inserted into a blood vessel, in order to puncture the target lesion in body tissue and thereby inject a specified reagent into the lesion through the inner hole provided in the needle-like tubular body.

In the above, some reagent injection devices having this structure are designed with two guide wires in such a way that the load from the reactive force generated by a needle-puncturing action is received by the two guide wires (e.g., Japanese Patent Laid-open No. 2003-250899).

To be specific, the reagent injection device has one guide wire extending out of the main tube (catheter main body) through an opening provided at the tip of the main tube. The other guide wire extends to the outside through an opening provided in the tube wall on a side of the main tube. In this reagent injection device, when the main tube is inserted into a blood vessel dividing into two branches, for example, the guide wire extending out of the opening at the tip of the main tube is inserted into one branch vessel, while the other guide wire extending out of the opening on a side of the main tube is inserted into the other branch vessel. At this time, the balloon attached externally to the main tube is inflated. In this condition, the needle of the needle-like tubular body is projected out of the main tube and caused to puncture the target lesion in body tissue.

As explained above, the reagent injection device allows the reactive force generated when the needle punctures the target body tissue to be received by the two guide wires inserted separately into the two branch vessels. The balloon also prevents displacement of the main tube inside the blood vessel. These actions ultimately prevent rotation of the main tube about its axis center, which rotation could otherwise occur due to the reactive force generated when the needle punctures the target body tissue and also due to other forces resulting from a kink of the needle-like tubular body, and so on. Consequently, the needle can reliably and smoothly reach a desired depth in the target body tissue. At the same time, the puncturing location of the needle in the body tissue can be maintained in a stable manner.

DISCLOSURE OF INVENTION

The inventors began research with the aim of obtaining a reagent injection device or devices as described above. In the process, the balloon was removed to implement the aforementioned structures in a smaller reagent injection device. As a result, it was found that without the balloon it was difficult to sufficiently prevent the rotation of the main tube in the circumferential direction caused by the reactive force generated when the needle punctures the target body tissue and also by other forces resulting from a kink of the needle-like tubular body, and so on. Accordingly, it was revealed that a reagent injection device having two guide wires alone might not fully provide the desired effect of smoothly puncturing the target body tissue with the needle at a specified position to a specified depth.

In addition, conventional reagent injection devices have a total of four lumens extending almost throughout their entire length. These four lumens in the main tube include three lumens, each accommodating a needle-like tubular body and each of two guide wires, and another lumen through which a liquid for inflating the balloon is passed. The inventors considered that a reagent injection device of this structure could not provide a sufficiently thin diameter or sufficiently small size that would make it easier to insert the reagent injection device into the human body.

Furthermore, conventional reagent injection devices presented another problem of making it difficult to accurately grasp the inserted depth of the needle inside the target body tissue when the tissue is punctured with the needle.

The present invention was completed against the backdrop explained above. A first problem to be solved by an embodiment of the present invention is to provide an injection device that can be made thinner or smaller and is able to reliably puncture a specified position in the target body tissue with the needle. A second problem to be solved by an embodiment of the present invention is to provide an injection device that allows the user to accurately grasp the inserted depth of the needle when the target body tissue is punctured with the needle in a reliable manner.

To solve the first problem, the injection device proposed by an embodiment of the present invention adopts a structure that comprises: a flexible main tube insertable into the human body; a tubular body movably inserted into the main tube and having a tip that projects out of the main tube to enable injection of a reagent into the human body; a first guide wire movably inserted into the main tube and extending out of the main tube in the axial direction of the main tube; a second guide wire movably inserted into the main tube and extending out of the main tube in the direction intersecting with the axial direction of the main tube; and a support tube provided in the main tube, having a free tip, and supporting the second guide wire.

To solve the second problem, the injection device proposed by an embodiment of the present invention adopted a structure that comprises: a flexible main tube insertable into the human body; a tubular body movably inserted into the main tube and having a tip that projects out of a projection aperture provided in the main tube to enable injection of a reagent into the human body; a main-body main marker made of radio-opaque material, provided at a position a specified distance rearward of the projection aperture in the main tube in the direction in which the main tube is inserted into the human body; a tubular-body first marker made of radio-opaque material, provided on the tubular body at a position away from the tip of the tubular body by the distance corresponding to the distance from the projection aperture in the main tube to the main-body main marker; and a tubular-body second marker made of radio-opaque material, provided on the tubular body at at least one location arranged at a specified interval from the tubular-body first marker at rear of the tubular-body first marker in the projection direction of the tubular body.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF DRAWINGS

These and other features of this invention will now be described with reference to the drawings of preferred embodiments which are intended to illustrate and not to limit the invention. The drawings are oversimplified for illustrative purposes.

DESCRIPTION OF THE SYMBOLS IS AS FOLLOWS

Figure 1:
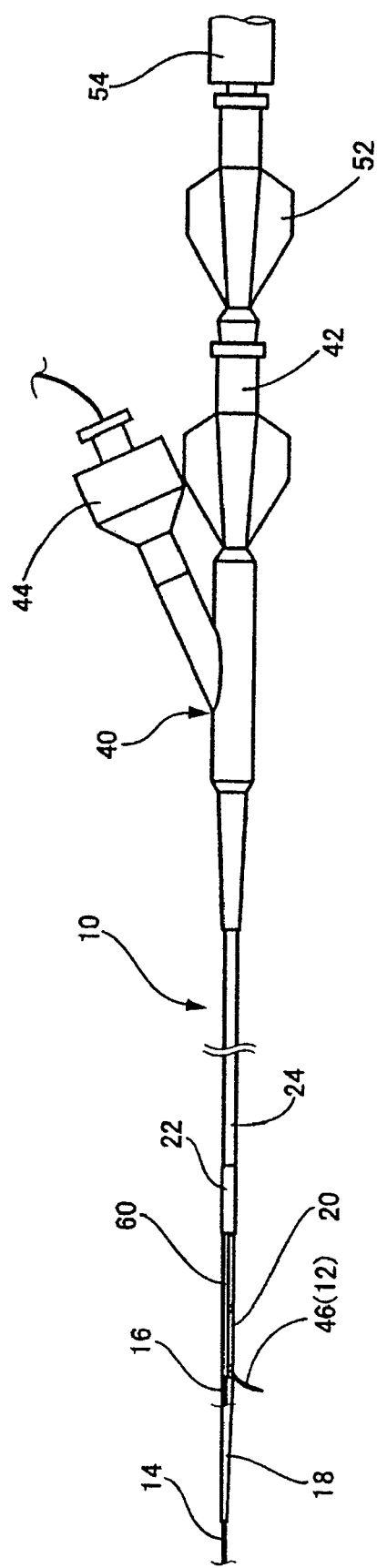
FIG. 1 is an explanatory drawing showing a front view of an embodiment of a reagent injection device having a structure conforming to the present invention.

| 10 | Main tube | 12 | Needle-like tubular body |
|---|---|---|---|
| 14 | First guide wire | 16 | Second guide wire |
| 26 | Lumen for first guide wire | 28 | First opening |
| 30 | Lumen for needle-like tubular body | 32 | Projection aperture |
| 34 | Lumen for second guide wire | 36 | Second opening |
| 38 | Third opening | 46 | Needle |
| 56 | Main-body marker tube | 58 | Needle marker tube |
| 60 | Support tube | 62 | Reinforcement tube |
| 64 | Cardiac muscle | 66 | Main vessel |
| 68 | Branch vessel | 72 | Cover tube |
| 74 | Outer tube | 76 | Inner tube |
| 86, 88 | Engagement surfaces | | |

BEST MODE FOR CARRYING OUT THE INVENTION

The present invention can be practiced in various ways including, but not limited to, embodiments described below, wherein numerals used in the drawings are used solely for the purpose of ease in understanding of the embodiments which should not be limited to the numerals. Further, in the present specification, different terms or names may be assigned to the same element, and in that case, one of the different terms or names may functionally or structurally overlap or include the other or be used interchangeably with the other.

In an embodiment, an injection device comprises: (i) a flexible main tube (e.g., 10) insertable into the human body; (ii) a tubular body (e.g., 12) movably inserted into the main tube and having a tip (e.g., 46) that projects out of the main tube to enable injection of a reagent into the human body; (iii) a first guide wire (e.g., 14) movably inserted into the main tube and extending out of the main tube in an axial direction of the main tube; (iv) a second guide wire (e.g., 16) movably inserted into the main tube and extending out of the main tube in a direction intersecting with the axial direction of the main tube; and (v) a support tube (e.g., 60) provided in the main tube, having a free tip, and supporting the second guide wire.

The above embodiment includes, but is not limited to, the following embodiments:

The support tube (e.g., 60) may comprise a base part (e.g., 62) and a tip part which is more flexible than the base part. The support tube (e.g., 60) may have a length of about 20 mm to about 40 mm.

The injection device may further comprise an external member (e.g., 72) Enclosing the main tube in an axially movable manner and coupling the main tube (e.g., 10) and the support tube (e.g., 60) at a distal end of the external member by axial movement of the external member, wherein a length of a flexible portion of the support tube is adjustable by the axial movement of the external member in accordance with a placement position of the distal end of the external member enclosing the main tube and the support tube.

The main tube may comprise: an outer tube (e.g., 74) having an inner cavity (e.g., 78); and an inner tube (e.g., 76) axially movable inside the inner cavity of the outer tube, wherein the second guide wire (e.g., 16) is inserted into the outer tube and the support tube (e.g., 60) is installed in the outer tube, and wherein the tubular body (e.g., 12) and the first guide wire (e.g., 14) are inserted into the inner tube and the tubular body (e.g., 2) and the first guide wire (e.g., 14) are projectable out of the inner tube.

The outer tube and the inner tube may be relatively movable in a circumferential direction. The injection device may further comprise an engagement portion (e.g., 88) where an inner periphery surface (e.g., 78) of the inner cavity of the outer tube and an outer periphery surface (e.g., 86) of the inner tube are engaged with each other to inhibit relative movement of the outer tube and the inner tube in a circumferential direction.

The injection device may further comprise an inflatable/deflatable balloon in the main tube. Alternatively, the main tube may comprise no inflatable/deflatable balloon.

In another embodiment, an injection device comprises: (i) a flexible main tube (e.g., 10) insertable into the human body and having a first lumen (e.g., 30), a second lumen (e.g., 26), and a third lumen (e.g., 34); (ii) a tubular body (e.g., 12) movably inserted into the first lumen and having a tip (e.g., 46) that projects through a projection aperture e.g., 32) provided in the main tube to enable injection of a reagent into the human body; (iii) a first guide wire (e.g., 14) movably inserted into the second lumen (e.g., 26) and extending, in an axial direction of the main tube (e.g., 10), through a first opening (e.g., 28) provided near a tip of the main tube; (iv) a second guide wire (e.g., 16) movably inserted into the third lumen (e.g., 34) and extending, in a direction intersecting with the axial direction of the main tube, through a second opening (e.g., 36) provided in a wall of the main tube (e.g., 10); and (v) a support tube (e.g., 60) provided in the main tube, communicated with the second opening (e.g., 36), having a free tip, and supporting the second guide wire.

The above embodiment includes, but is not limited to, the following embodiments:

The main tube (e.g., 10) may have a third opening (e.g., 38) through which the first guide wire (e.g., 14) is inserted into the second lumen (e.g., 26) or extended out of the second lumen, wherein the main tube has a first main part (e.g., 24) which has the first lumen (e.g., 30) and the third lumen (e.g., 34), but not the second lumen (e.g., 26), and which is provided at a position rearward of the third opening (e.g., 38) with respect to a direction in which the main tube is inserted into the human body.

The main tube may have a second main part (e.g., 20) which has the first Lumen (e.g., 30) and the second lumen (e.g., 26), but not the third lumen (e.g., 34), and which Is provided at a position forward of the second opening (e.g., 36) with respect to the direction in which the main tube is inserted into the human body.

The third opening (e.g., 38) may be formed at a position rearward of the second opening (e.g., 36) with respect to the direction in which the main tube is inserted into the human body, and wherein the main tube has a third main part (e.g., 22) which has the first lumen (e.g., 30), the second lumen (e.g., 26) and the third lumen (e.g., 34), and which is provided at a position between the second opening (e.g., 36) and the third opening (e.g., 38).

The main tube may have a fourth main part (e.g., 18) which has the second lumen (e.g., 26) only, and is provided at a position forward of the projection aperture (e.g., 32) with respect to the direction in which the main tube is inserted into the human body.

In still another embodiment, an injection device comprises: (i) a flexible main tube (e.g., 10) insertable into the human body; (ii) a tubular body (e.g., 12) movably inserted into the main tube and having a tip (e.g., 46) that projects through a projection aperture (e.g., 32) provided in the main tube to enable injection of a reagent into the human body; (iii) a main-body main marker (e.g., 56*b*) made of radio-opaque material, provided at a position rearward, at a specified distance, of the projection aperture (e.g., 32) in the main tube with respect to a direction in which the main tube is inserted into the human body; (iv) a tubular-body first marker (e.g., 58*a*) made of radio-opaque material, provided on the tubular body at a position away from the tip of the tubular body by a distance corresponding to the distance from the projection aperture in the main tube to the main-body main marker; and (v) a tubular-body second marker (e.g., 58*b*, 58*c*) made of radio-opaque material, provided on the tubular body at at least one location arranged at a specified interval from the tubular-body first marker at rear of the tubular-body first marker with respect to a projection direction of the tubular body.

The injection device may further comprise a main-body sub marker (e.g., 56*a*) made of radio-opaque material, provided near the projection aperture in the main tube.

In still another embodiment, an injection device comprises: (i) a flexible main tube (e.g., 10) insertable into the human body; (ii) a tubular body (e.g., 12) movably inserted into the main tube and having a tip (e.g., 46) that projects out of the main tube to enable injection of a reagent into the human body; (iii) a first guide wire (e.g., 14) movably inserted into the main tube and extending out of the main tube in an axial direction of the main tube; (iv) a second guide wire (e.g., 16) movably inserted into the main tube and extending out of the main tube in a direction intersecting with the axial direction of the main tube; and (v) a support tube (e.g., 60) provided in the main tube, having a free tip, supporting the second guide wire, and comprising a base part (e.g., 62) and a tip part that is more flexible than the base part.

In further another embodiment, an injection device comprises: (i) a flexible main tube (e.g., 10) insertable into the human body and having a first lumen (e.g., 30), a second lumen (e.g., 26), and a third lumen (e.g., 34); (ii) a tubular body (e.g., 12) movably inserted into the first lumen and having a tip (e.g., 46) that projects through a projection aperture (e.g., 32) provided in the main tube to enable injection of a reagent into the human body; (iii) a first guide wire (e.g., 14) movably inserted into the second lumen and extending, in an axial direction of the main tube, through a first opening (e.g., 28) provided near the tip of the main tube; (iv) a second guide wire (e.g., 16) movably inserted into the third lumen and extending, in a direction intersecting with the axial direction of the main tube, through a second opening (e.g., 36) provided in a wall of the main tube; (v) a third opening (e.g., 38) provided in the main tube and through which the first guide wire is inserted into the second lumen or extended out of the second lumen; (vi) a first main body (e.g., 24) having the first lumen (e.g., 30) and the third lumen (e.g., 34), but not the second lumen (e.g., 26), provided in the main tube at a position rearward of the third opening (e.g., 38) with respect to a direction in which the main tube is inserted into the human body; and (vii) a support tube (e.g., 60) provided in the main tube, communicated with the second opening (e.g., 36), having a free tip, and supporting the second guide wire (e.g., 16).

In all of the aforesaid embodiments, any element used in an embodiment can interchangeably be used in another embodiment unless such a replacement is not feasible or causes adverse effect. Further, the present invention can equally be applied to apparatuses and methods.

To further explain the specifics of the present invention, the structures of reagent injection devices pertaining to the present invention are explained in details with reference with drawings and preferred embodiments. The drawings and preferred embodiments are not intended to limit the present invention. In the embodiments, dimensional numerals are indicated. These dimensional numerals may vary from 30% to 300%, from 50% to 200%, or from 70% to 150% thereof depending on the particular configuration.

First, FIG. 1 illustrates the front view of one embodiment of a reagent injection device having a structure conforming to the present invention, which is a reagent injection catheter used to inject reagents into lesions in the cardiac muscle. In FIG. 1, the numeral 10 indicates a main tube comprising a long tubular body, with a needle-like tubular body (12), a first guide wire (14) and a second guide wire (16) inserted into the main tube in an axially movable manner.

The main tube (10) also has an appropriate thickness and length that make the tube insertable into the blood vessels extending from the thighs and wrists to the heart over the entire lengths of these vessels. This tube is formed using polyethylene resin. This material helps maintain an optimal balance of sufficient flexibility and appropriate rigidity, thus allowing the tube to be inserted smoothly into the meandering blood vessels.

In the above, materials that can comprise the main tube (10) are not limited, and any material can be used as long as it can add flexibility to the main tube (10). In addition to the material mentioned above, for example, polyamides and other synthetic resin materials, Ni—Ti alloys and other super-elastic alloy materials, or stainless steels and other metal materials can be used alone or in suitable combinations. Also, a stainless steel wire may be sandwiched and buried between the tubular inner layer and outer layer having a specified flexible resin layer structure.

Figure 2:
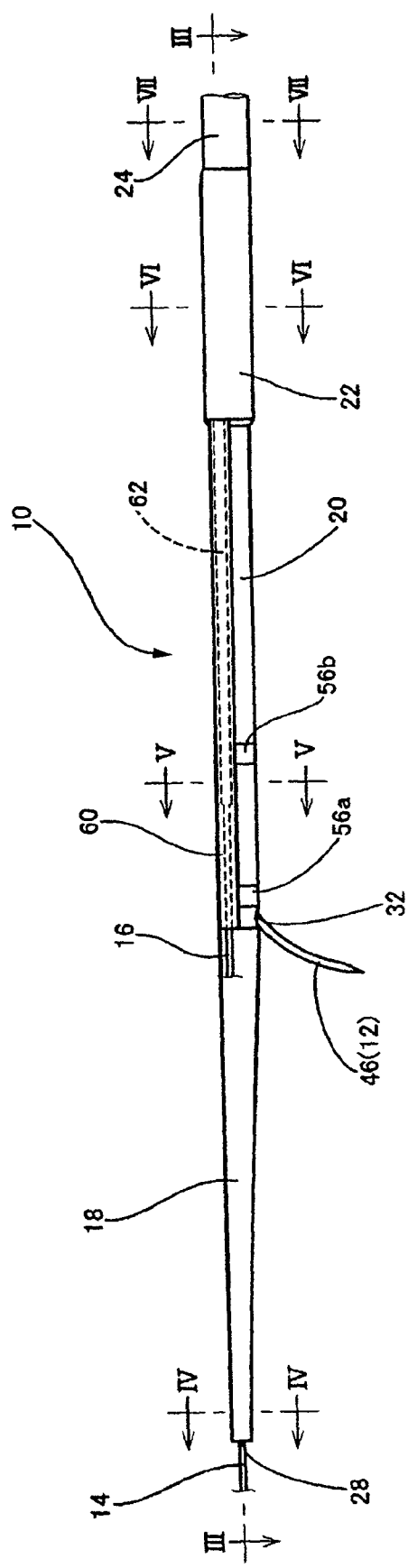
FIG. 2 is an explanatory drawing showing an enlarged view of a part of FIG. 1

As evident from FIGS. 1 and 2, the main tube (10) has a tip (18) comprising a fourth main part, a first intermediate section (20) comprising a second main part, and a second intermediate section (22) comprising a third main part, with these three parts arranged in this order from the tip at the front end of the main tube (10) in the direction in which the main tube is inserted into the human blood vessels (left in FIGS. 1 and 2). In addition, the main tube (10) also has a base (24) comprising a first main part, which excludes the front end that comprises the above three parts (18, 20 and 22). To facilitate the understanding of the main tube (10) and the overall structure of the reagent injection catheter, the tip (18) side and base (24) side of the main tube (10) will be hereinafter referred to as the front side and rear side, respectively.

Also, the tip (18), first intermediate section (20), second intermediate section (22) and base (24) are separate, individually formed tubes. These four individually formed tubes that respectively comprise the tip (18), first intermediate section (20), second intermediate section (22) and base (24) are then bonded together. In other words, the four tubes are arranged in a straight line with the adjoining tubes contacting each other, and in this condition the respective joints are melted and welded. As a result, the main tube (10) is formed as an integral piece comprising the tip (18), first intermediate section (20), second intermediate section (22) and base (24).

Figure 3:
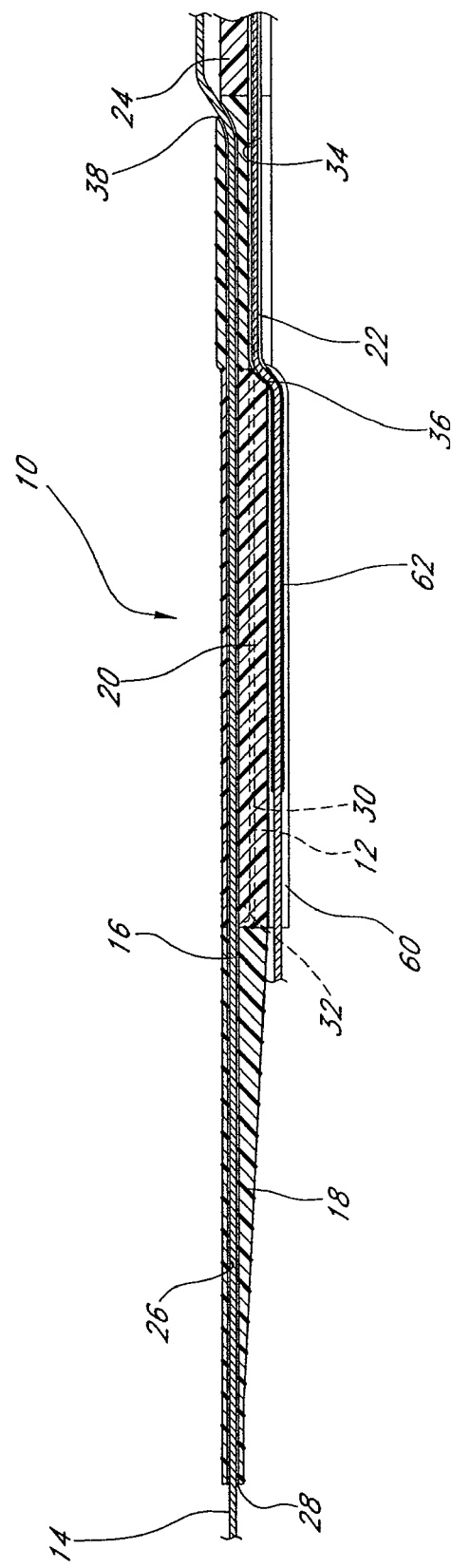
FIG. 3 is an explanatory drawing showing a III-III section view of FIG. 2.
Figure 4:
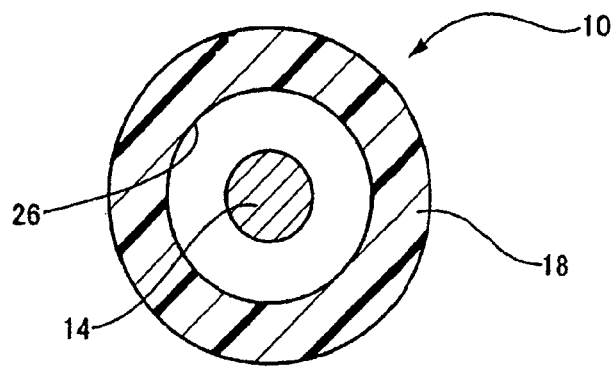
FIG. 4 is an explanatory drawing showing an enlarged IV-IV section view of FIG. 2.

As shown in FIGS. 2 through 4, the exterior of the tip (18) of the main tube (10) has a roughly tapered shape in which the diameter of the tip (18) gradually decreases toward the front side. At this tip (18), the outer diameter of the small end is set to, say, approx. 0.77 mm, while the outer diameter of the large end is set to, say, approx. 1.0 mm.

Inside the tip (18), only a first guide wire lumen (26) comprising a second lumen is formed to extend continuously in the axial direction. Furthermore, the front end face of this tip (18) has a first opening (28), and the first guide wire lumen (26) opens forward through this first opening (28). Here, the diameter of the first guide wire lumen (26) is set to, say, approx. 0.45 mm.

Figure 5:
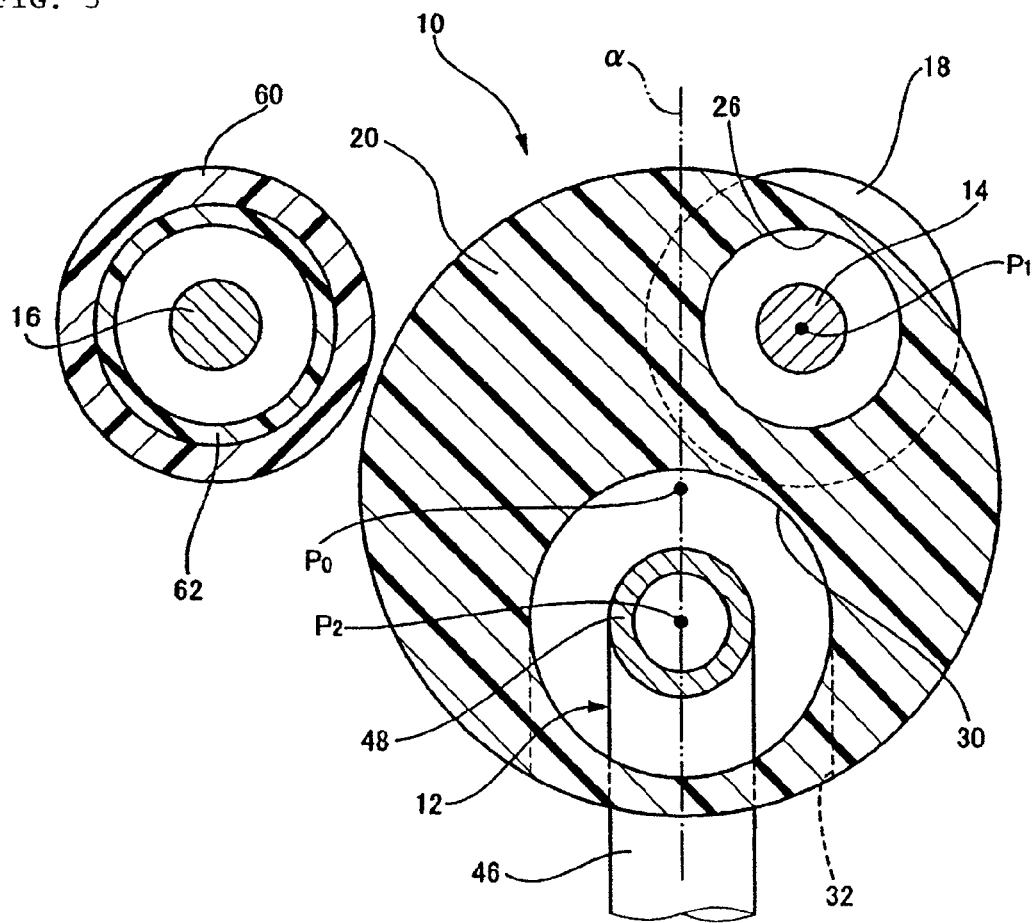
FIG. 5 is an explanatory drawing showing an enlarged V-V section view of FIG. 2.

On the other hand, the first intermediate section (20) has a cylindrical outer periphery surface extending longitudinally by maintaining a constant diameter, as shown in FIGS. 2, 3 and 5. The outer diameter of the first intermediate section (20) is set to, say, approx. 1.41 mm.

Inside the first intermediate section (20), the first guide wire lumen (26) extending from the tip (18), and a needle-like tubular body lumen (30) comprising a first lumen and having a larger diameter than the first guide wire lumen (26), are formed in such a way that they extend in parallel and continuously in the axial direction. The diameter of the needle-like tubular body lumen (30) is set to, say, approx. 0.75 mm.

The first guide wire lumen (26) and needle-like tubular body lumen (30) formed inside the first intermediate section (20) are arranged at positions that are respectively offset by specified dimensions in the radial direction on both sides of the center axis ($P_0$) of the first intermediate section (20). In addition, the first guide wire lumen (26) is arranged in such a way that its center axis ($P_1$) extends in parallel with, but away from, plane α (indicated by the two-dot chain line in FIG. 5) that includes the center axis ($P_0$) of the first intermediate section (20) and the center axis ($P_2$) of the needle-like tubular body lumen (30).

The tube wall at the end of this first intermediate section (20) on the tip (18) side has a projection aperture (32) at which the needle-like tubular body lumen (30) opens to the outside. This projection aperture (32) also opens onto the aforementioned plane α that includes the center axes ($P_0$ and $P_2$) of the first intermediate section (20) and needle-like tubular body lumen (30) and extends vertically, or in the direction intersecting with the longitudinal direction (vertical direction in FIG. 5), wherein the projection aperture (32) opens in the same direction as the orientation of the vertical line drawn downward from the center axis ($P_0$) of the first intermediate section (20) to the center axis ($P_2$) of the needle-like tubular body lumen (30) (downward in FIG. 5). In other words, the needle-like tubular body lumen (30) opens downward through the projection aperture (32) at the front end of the first intermediate section (20).

Figure 6:
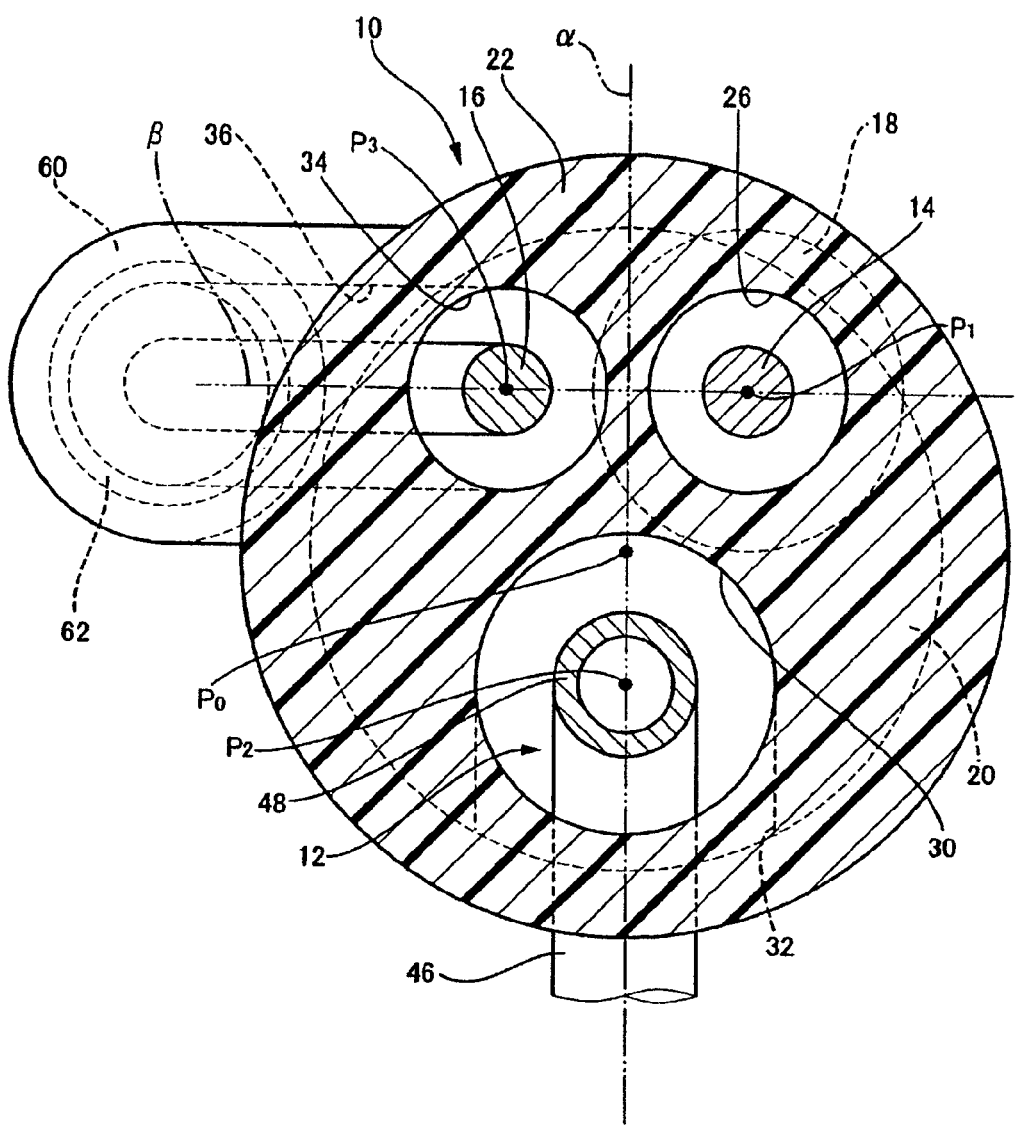
FIG. 6 is an explanatory drawing showing an enlarged VI-VI section view of FIG. 2.

On the other hand, the second intermediate section (22) has a tubular outer periphery surface whose diameter is larger by a specified dimension than that of the first intermediate section (20), as evident from FIGS. 2, 3 and 6. The second intermediate section (22) is also positioned coaxially with the first intermediate section (20). By the way, the outer diameter of the second intermediate section (22) is set to, say, approx. 1.66 mm.

Inside the second intermediate section (22), the first guide wire lumen (26) extending from the tip (18) and first intermediate section (20), the needle-like tubular body lumen (30) extending from the first intermediate section (20), and a second guide wire lumen (34) comprising a third lumen and having roughly the same diameter as the first guide wire lumen (26), are formed in such a way that they extend in parallel and continuously in the axial direction. By the way, the diameter of the second guide wire lumen (34) is set to, say, approx. 0.45 mm.

Of these three lumens (26, 30 and 34), the first guide wire lumen (26) and needle-like tubular body lumen (30) are arranged in the second intermediate section (22) based on the same layout as in the first intermediate section (20). The second guide wire lumen (34) is arranged in a position where plane β (indicated by the two-dot chain line in FIG. 6) that includes its center axis ($P_3$) and the center axis ($P_1$) of the first guide wire lumen (26) crosses at right angles, at the midpoint of the straight line connecting $P_3$ and $P_1$, with plane α (indicated by the two-dot chain line in FIG. 6) that includes the center axis ($P_0$) of the first intermediate section (20) and the center axis ($P_2$) of the needle-like tubular body lumen (30).

In addition, the tube wall at the end of the second intermediate section (22) on the tip (18) side has a second opening (36) at which the second guide wire lumen (34) opens to the outside. This second opening (36) also opens onto plane β that includes the center axes ($P_1$ and $P_3$) of the first guide wire lumen (26) and second guide wire lumen (34) and extends laterally, or in the direction (lateral direction in FIG. 6) roughly perpendicular to the longitudinal direction and vertical direction. In other words, it opens roughly in the same direction as the orientation of the perpendicular line drawn leftward from the center axis ($P_1$) of the first guide wire lumen (26) to the center axis ($P_3$) of the second guide wire lumen (34) (downward direction in FIG. 3, and leftward direction in FIG. 6).

Additionally, the tube wall at the end of this second intermediate section (22) on the opposite side (base (24) side) of the tip (18) has a third opening (38) at which the first guide wire lumen (26) opens to the outside. This third opening (38) opens onto the aforementioned plane β roughly in the same direction as the orientation of the perpendicular line drawn rightward from the center axis ($P_3$) of the second guide wire lumen (34) to the center axis ($P_1$) of the first guide wire lumen (26) (upward direction in FIG. 3, and rightward direction in FIGS. 6 and 7) (refer to FIG. 7).

Hence, at the front end (end on the tip (18) side) of the second intermediate section (22), the second guide wire lumen (34) opens, through the second opening (36), in the leftward direction when viewed toward the front side of the device. At the rear end (end on the base (24) side) of the second intermediate section (22), the first guide wire lumen (26) opens, through the third opening (38), in the rightward direction when viewed toward the front side of the device.

Figure 7:
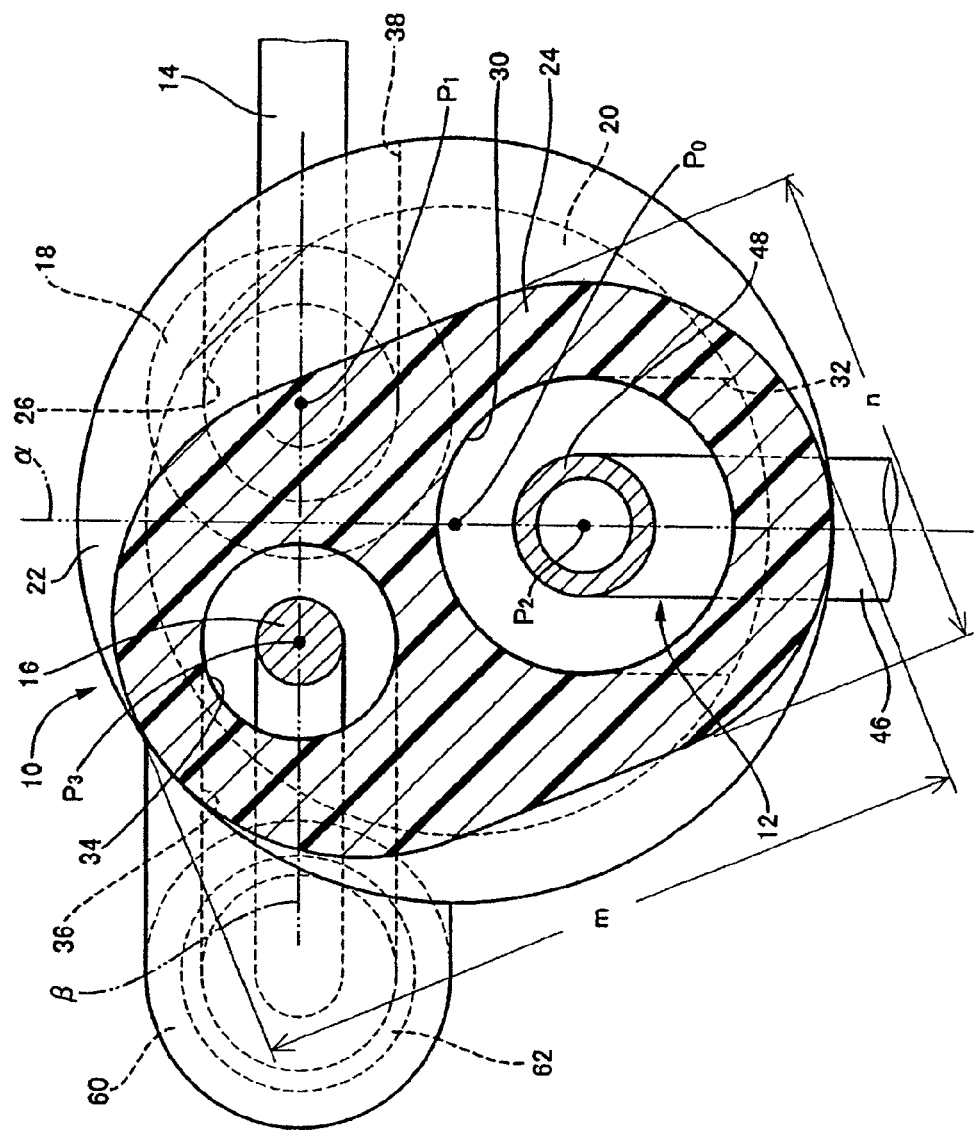
FIG. 7 is an explanatory drawing showing an enlarged VII-VII section view of FIG. 2.

Furthermore, the base (24) has a tubular outer periphery surface having an oval cross-section, as shown in FIGS. 2, 3 and 7. The oval cross-section shape of this base (24) has a smaller cross-section area than that of the first and second intermediate sections (20 and 22). In other words, its longer diameter (dimension indicated by m in FIG. 7) is roughly the same as the outer diameter of the first and second intermediate sections (20 and 22) having a round cross-section, and is set to, say, approx. 1.54 mm. On the other hand, its shorter diameter (dimension indicated by n in FIG. 7) is smaller than the outer diameter of these intermediate sections and set to, say, approx. 1.28 mm.

Inside this base (24), the needle-like tubular body lumen (30) and second guide wire lumen (34) extending from the first and second intermediate sections (20 and 22) are formed in such a way that they extend in parallel and continuously in the axial direction. Also, these two lumens (30 and 34) are arranged inside the base (24) in such a way that they correspond to their layout in the first and second intermediate sections (20 and 22).

Furthermore, the rear end face of this base (24) has two openings (not illustrated) at which the needle-like tubular body lumen (30) and second guide wire lumen (34) open to the rear side, respectively. As shown in FIG. 1, this rear end of the base (24) has a branching socket (40) having a first connection part (42) and a second connection part (44). These first and second connection parts (42 and 44) in the branching socket (40) are connected respectively to the two openings provided in the rear end face of the base (24).

Thus, the reagent injection catheter provided in this embodiment has the needle-like tubular body lumen (30) formed to extend continuously in the axial direction inside the main tube (10) through its first intermediate section (20), second intermediate section (22) and base (24). This needle-like tubular body lumen (30) then opens to the outside through the projection aperture (32) provided in the tube wall at the front end of the first intermediate section (20) and also through the first connection part (42) in the branching socket (40) connected to the rear end of the base (24).

Also, the first guide wire lumen (26) is formed to extend continuously in the axial direction inside the main tube (10) through its tip (18), first intermediate section (20) and second intermediate section (22). This first guide wire lumen (26) then opens to the outside through the first opening (28) provided in the front end face of the tip (18) and also through the third opening (38) provided in the tube wall at the rear end of the second intermediate section (22).

Furthermore, the second guide wire lumen (34) is formed to extend continuously in the axial direction inside the main tube (10) through its second intermediate section (22) and base (24). This second guide wire lumen (34) then opens to the outside through the second opening (36) provided in the tube wall at the front end of the second intermediate section (22) and also through the second connection part (44) in the branching socket (40) connected to the rear end of the base (24).

Here, as mentioned earlier the main tube (10) is formed from four integrally bonded tubes that respectively comprise the four parts of the main tube (10); namely the tip (18), first intermediate section (20), second intermediate section (22) and base (24). Among them, the tubes comprising the second intermediate section (22) and base (24) have the same diameter or a longer diameter. The tube comprising the tip (18) is a cylindrical tube whose outer diameter is roughly the same as that of the front small-diameter end of the tip (18). Furthermore, the tube comprising the first intermediate section (20) has the same outer periphery surface shape as the tubular shape with an oval cross-section characterizing the base (24). In the process of welding or bonding these four tubes by applying heat, the tubes comprising the tip (18) and first intermediate section (20) are deformed in such a way that the tip (18) and first intermediate section (20) have the aforementioned circular outer periphery shape.

In other words, when producing the main tube (10) used in this embodiment, first the tube comprising the tip (18) and the tube comprising the first intermediate section (20) are arranged in such a way that parts of the first guide wire lumen (26) passing through the two tubes form a continuous passage. Then, the tube comprising the first intermediate section (20) and the tube comprising the base (24) are placed with the tube comprising the second intermediate section (22) sandwiched in between. These three component tubes are arranged in such a way that parts of the needle-like tubular body lumen (30) passing through the three tubes form a continuous passage. With all tubes arranged in this condition, the following layout is achieved: the tube comprising the first intermediate section (20) and the tube comprising the second intermediate section (22) are arranged in such a way that their pars of the first guide wire lumen (26) form a continuous passage; the tube comprising the second intermediate section (22) and the tube comprising the base (24) are arranged in such a way that their parts of the second guide wire lumen (34) form a continuous passage; and the tube comprising the first intermediate section (20) and the tube comprising the base (24) are arranged in such a way that they have different phases in the circumferential direction.

Next, thus arranged four tubes are bonded with each other by applying heat. In this bonding process, the tube comprising the tip (18) is deformed into a tapered barrel shape having a diameter gradually decreasing toward the front end. The tube comprising the first intermediate section (20) is also deformed in a cylindrical shape having a diameter smaller than that of the second intermediate section (22).

This way, the front end of the main tube (10) comprising the tip (18), first intermediate section (20) and second intermediate section (22) is formed as a single tapered shape. The remaining part of the main tube (10) excluding the front end, or the part comprising the base (24), is thinner than the first intermediate section (20) or second intermediate section (22). As a result, the entire main tube (10) has a smaller diameter or size that is more advantageous compared with the main body structures of conventional reagent injection catheters.

In this embodiment, of the aforementioned three lumens (30, 26 and 34) provided in the main tube (10), the needle-like tubular body lumen (30) has the needle-like tubular body (12) inserted in itself, through the first connection part (42) in the branching socket (40), in an axially movable manner, as shown in FIGS. 1 and 3. Also, the first guide wire lumen (26) has a first guide wire (14) inserted in itself, through the third opening (38), in an axially movable manner, and this first guide wire (14) is then extended to the outside through the first opening (28). Furthermore, the second guide wire lumen (34) has a second guide wire (16) inserted in itself, through the second connection part (44) in the branching socket (40), in an axially movable manner, and this second guide wire (16) is then extended to the outside through the second opening (36).

Figure 8:
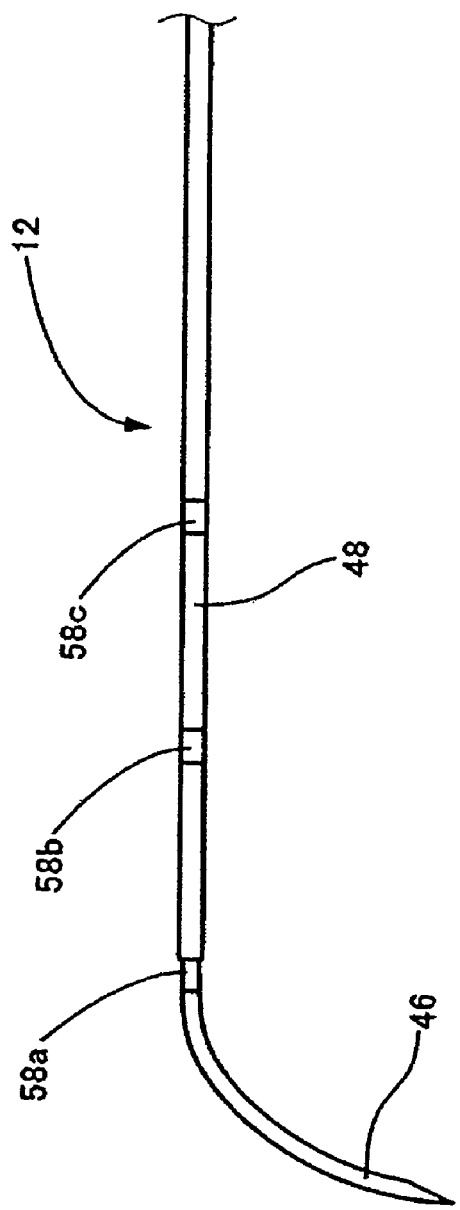
FIG. 8 is an explanatory drawing showing a front view of the needle-like tubular body inserted into the main tube of the reagent injection device shown in FIG. 1.

As evident from FIG. 8, the overall needle-like tubular body (12) inserted into the needle-like tubular body lumen (30) comprises a thin flexible tube. Also, the tip of this tubular body forms a sharp needle (46). The remaining part of the needle-like tubular body (12), excluding the tip having this needle (46), forms a reagent feed channel (48) comprising a thin tube longer than the main tube (10). Here, the outer diameter of the needle (46) is set to, say, approx. 0.4 mm. On the other hand, the outer diameter of the reagent feed channel (48) is set to, say, approx. 0.66 mm.

This reagent feed channel (48) in the needle-like tubular body (12) is made of, for example, polytetrafluoroethylene, polyimide or other flexible synthetic resin material. On the other hand, the needle (46) is made of, for example, Ni—Ti alloy or other super-elastic alloy material, stainless steel or other metal material, or other elastic material. This gives the needle-like tubular body (12) sufficient flexibility or elasticity, thus allowing it to be smoothly inserted into the needle-like tubular body lumen (30) in the main tube (10) that has been inserted into the meandering blood vessels, and moved axially.

Figure 9:
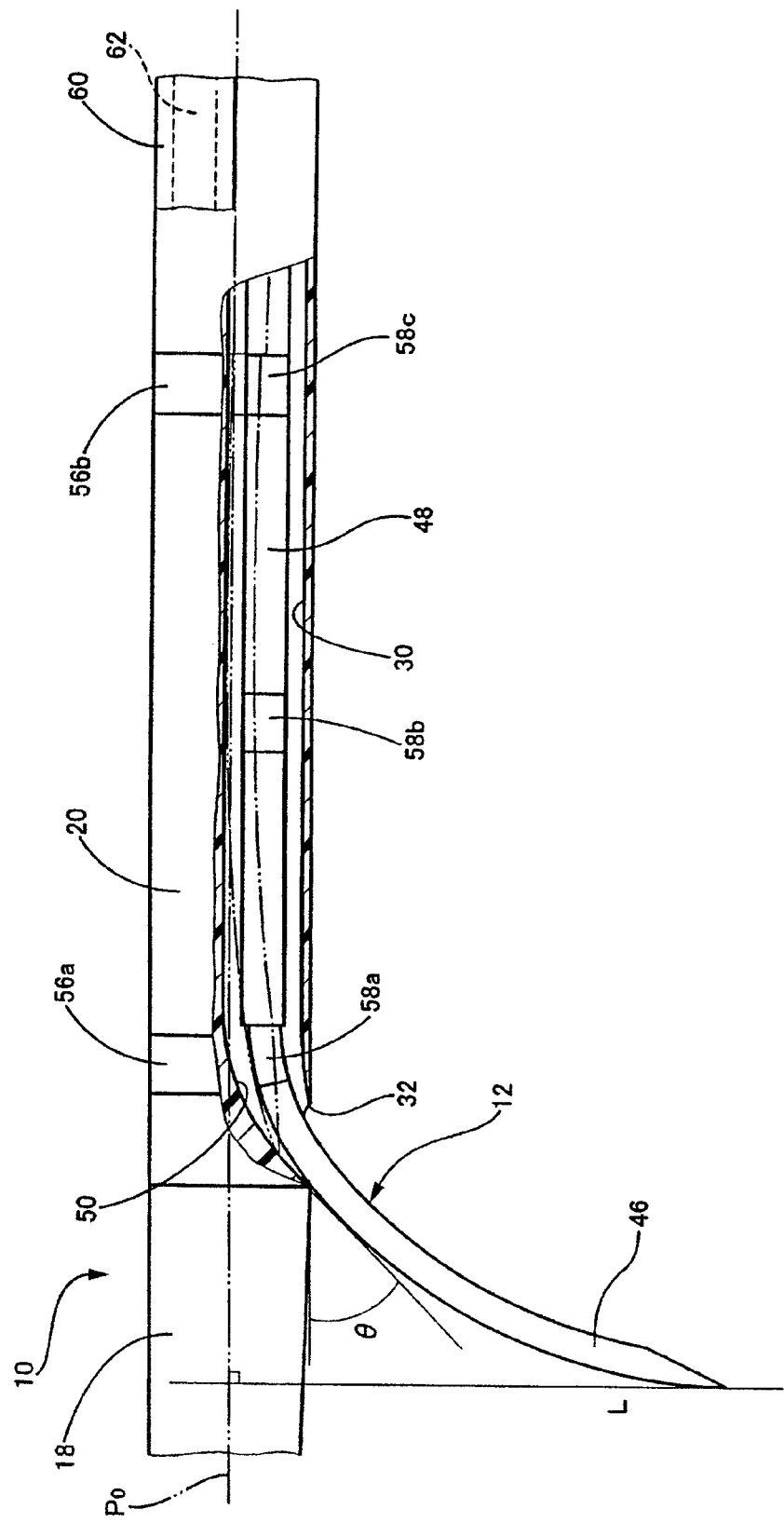
FIG. 9 is an explanatory drawing, including a cutout view, showing a partially enlarged section of the reagent injection device shown in FIG. 1.

Here, the inner periphery surface at the front end of the needle-like tubular body lumen (30) provides a guide surface (50) that comprises a convex surface curving toward the opening of the projection aperture (32), as shown in FIG. 9. The needle (46) also has a curved shape corresponding to the curved shape of this guide surface (50). For this reason, when the needle-like tubular body (12) is moved forward in the needle-like tubular body lumen (30) and the needle (46) eventually reaches the projection aperture (32) formed in the main tube (10), the needle (46) will be smoothly guided by the guide surface (50) toward the projection aperture (32). Thereafter, a further forward movement of the needle-like tubular body (12) will cause the needle (46) to project out of the projection aperture (32). This projection will also cause the needle (46) to puncture the cardiac muscle (refer to FIG. 13).

These curved shapes of the guide surface (50) of the needle-like tubular body lumen (30) and needle (46) are determined as deemed appropriate for the rigidity of the needle (46), for example, and other factors. Also, although the radii of curvature and other dimensions of the curves of the guide surface (50) and needle (46) are not specifically limited, it is desirable that when the curved pattern of the guide surface (50) and the curved shape of the needle (46) are combined and the needle (45) projects out of the projection aperture (32), the projection angle ($\theta$) becomes approx. 45° or more at the point where the two curves make contact with each other.

This way, when the needle (46) projects out of the projection aperture (32), tangential line L at the tip of the projected needle crosses, at right angles and at a position closer to the projection aperture (32), with the center axis ($P_0$) of the first intermediate section (20) comprising the main tube (10). Accordingly, the component force generated in The direction in which the needle-like tubular body (12) is inserted into the cardiac muscle (of the two vectors shown in FIG. 10, Vv and Vh, this component force corresponds to the size of Vv acting perpendicularly to the center axis ($P_0$) of the first intermediate section) can be kept sufficiently large. As a result, the needle (46) of the needle-like tubular body (12) can be inserted into the cardiac muscle more smoothly.

As shown in FIG. 1, this needle-like tubular body (12) has a connector (52) attached on one end of the reagent feed channel (48) on the opposite side of the needle (46). Furthermore, this connector (52) is connected to a syringe (54) of a known structure to be used as a reagent feeder. This way, a reagent containing an osteoblast or growth factor, such as bFGF (basic Fibroblast Growth Factor), VEGF (Vascular Endothelial Growth Factor) or HGF (Hepatocyte Growth Factor), can be introduced into the reagent feed channel (48) and discharged to the outside through the opening at the tip of the needle (46).

As evident from FIGS. 8 and 9, in the reagent injection catheter provided in this embodiment a main-body first marker tube (56a) (main-body sub marker) and a main-body second marker tube (56b) (main-body main marker) are placed over the main tube (10) at positions rearward of the projection aperture (32), with the former positioned near the projection aperture (32) and the latter at, say, 10 mm away from the projection aperture (32).

As for the needle-like tubular body (12), a needle first marker tube (58*a*) (tubular-body first marker) is affixed over the tubular body at, say, 10 mm or a slightly shorter distance away from the tip of the needle (46) toward the base (rearward with respect to the direction in which the needle-like tubular body (12) is inserted into the main tube (10)). In addition, a needle second marker tube (58*b*) (tubular-body second marker) and a needle third marker tube (58*c*) are also affixed over the needle-like tubular body (12) with an interval of, say, 4 mm between them, at positions closer to the base than the position where the needle first marker tube (58*a*) is placed. These two main-body marker rubes (56*a* and 56*b*) and three needle marker tubes (58*a*, 58*b* and 58*c*) all have a length of, say, approx. 1 mm, and are formed using, for example, gold, platinum, platinum-rhodium alloy or other radio-opaque materials.

This way, this reagent injection catheter allows for identification by X-ray fluoroscopy of the position of the main-body first marker tube (56*a*) affixed near the projection aperture (32) in the main tube (10), when the main tube (10) is inserted into a blood vessel. This allows for easy identification of the position of this projection aperture (32) in the blood vessel.

Also, when the needle-like tubular body (12) is moved forward inside the needle-like tubular body lumen (30) in the main tube (10) that has been inserted into a specified location in a blood vessel, it is possible to check by X-ray fluoroscopy if the needle first marker tube (58*a*) affixed closest to the tip of the needle-like tubular body (12) is overlapping with the main-body second marker tube (56*b*) affixed rearward of the projection aperture (32) in the main tube (10); namely, if the two are in the same position. This way, whether the tip of the needle (46) of the needle-like tubular body (12) has reached the projection aperture (32) formed in the main tube (10), or its proximity, can be easily identified.

When the needle-like tubular body (12) is moved further forward in this condition, X-ray fluoroscopy can be used to check if the needle second marker tube (58*b*) affixed closer to the base than the needle first marker tube (58*a*) is overlapping with the main-body second marker tube (56*b*) on the main tube (10); namely, if the two are in the same position. This way, whether a 5-mm section from the tip of the needle (46) of the needle-like tubular body (12) has projected from the projection aperture (32) in the main tube (10) can be identified.

Moreover, X-ray fluoroscopy can be used to check if the needle third marker tube (58*c*) affixed closer to the base than the needle second marker tube (58*b*) is overlapping with the main-body second marker tube (56*b*) on the main tube (10); namely, if the two are in the same position. This way, whether a 10-mm section from the tip of the needle (46) of the needle-like tubular body (12) has projected from the projection aperture (32) in the main tube (10) can be easily identified.

As explained above, in this embodiment the first guide wire (14) and second guide wire (16) are positioned in such a way that they extend side by side in the lateral direction through the second intermediate section (22) of the main tube (10), as shown in FIG. 3. Also, the two guide wires are extended forward and leftward through the first opening (28) and second opening (36), respectively. Furthermore, the needle (46) of the needle-like tubular body (12) projects out of the projection aperture (32) in the direction virtually perpendicular to the extension directions of the first guide wire (14) and second guide wire (16).

This way, the layout balance of the first guide wire (14), second guide wire (16) and needle-like tubular body (12) inside the main tube (10) is favorably enhanced. This effectively improves the moving operations of the first guide wire (14), second guide wire (16) and needle-like tubular body (12) inside the main tube (10), and consequently the reagent injection operation to be explained later.

By the way, the reagent injection catheter provided in this embodiment has a support tube (60) integrally formed with the main tube (10) in its second intermediate section (22) to extend forward, as shown in FIGS. 2 and 3. The second guide wire (16) extending through the second opening (36) in the second intermediate section (22) is inserted into this support tube (60) and thereby supported.

To be more specific, the support tube (60) comprises a thin cylindrical body made of urethane resin, for example. Its outer diameter is set to, say, approx. 0.8 mm, which is roughly the same as the outer diameter of the small-diameter end of the tip (18) of the main tube (10). This minimizes the diameter of the support tube (60) and adds sufficient flexibility and elasticity at the same time.

The length of this support tube (60) is preferably in a range of approx. 20 to 40 mm. This is because if the length is less than 20 mm, the tube will be too short to sufficiently support the second guide wire (16) and to effectively receive the puncturing reactive force of the needle-like tubular body (12) against the cardiac muscle. If the length of the support tube (60) exceeds 40 mm, the long support tube (60) may interfere with a smooth insertion of the main tube (10) into a blood vessel.

Therefore, it is desirable that the support tube (60) be set to a length of approx. 20 to 40 mm, in part to maintain a favorable level of operability when inserting the main tube (10) into a blood vessel, and in part to obtain a sufficient supporting force for the second guide wire (16) to effectively receive the puncturing reactive force of the needle-like tubular body (12). By the way, in this embodiment the length of this support tube (60) is set within the above favorable range at a level roughly the same as the length from the second opening (36) to the projection aperture (32) in the main tube (10). This allows for easy identification of the position of the projection aperture (32) by way of checking the position of the support tube (60) tip.

Therefore, in this case this support tube (60) is positioned in such a way that it extends forward alongside the first intermediate section (20) of the main tube (10) in parallel with the main tube (10). Then, while its front end is free, its rear end face is integrated with the periphery of the second opening (36) provided in the second intermediate section (22). In other words, the support tube (60) is formed in such a way that it branches from the tube wall at the front end of the second intermediate section (22) comprising the main tube (10) and then extends integrally forward, while its inner hole continues into the second guide wire lumen (34) through the second opening (36).

Also, in this embodiment a reinforcement tube (62) is inserted into the support tube (60) of the structure explained above. This reinforcement tube (62) comprises a cylindrical body made of polyimide, for example. The inner diameter of the reinforcement tube (62) is set in such a way that the second guide wire (16) is easily movable inside the tube in the axial direction. The length of the reinforcement tube (62) is set to approx. two-thirds the length of the support tube (60). This reinforcement tube (62), while inserted in the support tube

(60) at the base side (rear end side of the support tube (60)), is integrated with the periphery of the second opening (36) provided in the second intermediate section (22).

Thus the support tube (60) has a dual-wall structure at its base side where the reinforcement tube (62) is inserted. This increases the rigidity of the dual-walled base part of the support tube (60) to a level higher than the rigidity of the tube tip. As a result, the tip of the support tube (60) having no reinforcement tube (62) on the inside becomes more flexible than the base part in which the reinforcement tube (62) is placed.

Therefore, the second guide wire (16) that extends from the second guide wire lumen (34) through the second opening (36) in this second intermediate section (22) is inserted into the support tube (60) having such structure and integrally formed with the second intermediate section (22) of the main tube (10), wherein the base part of the second guide wire (16) is inserted into the reinforcement tube (62) in an axially movable manner. This way, the part of the second guide wire (16) extending from the second opening (36) is supported by the support tube (60) and reinforcement tube (62).

Next, how to inject a specified reagent into the target lesion in the cardiac muscle, such as a nearly or substantially necrotic part, using the reagent injection catheter provided in this embodiment, is explained.

Figure 11:
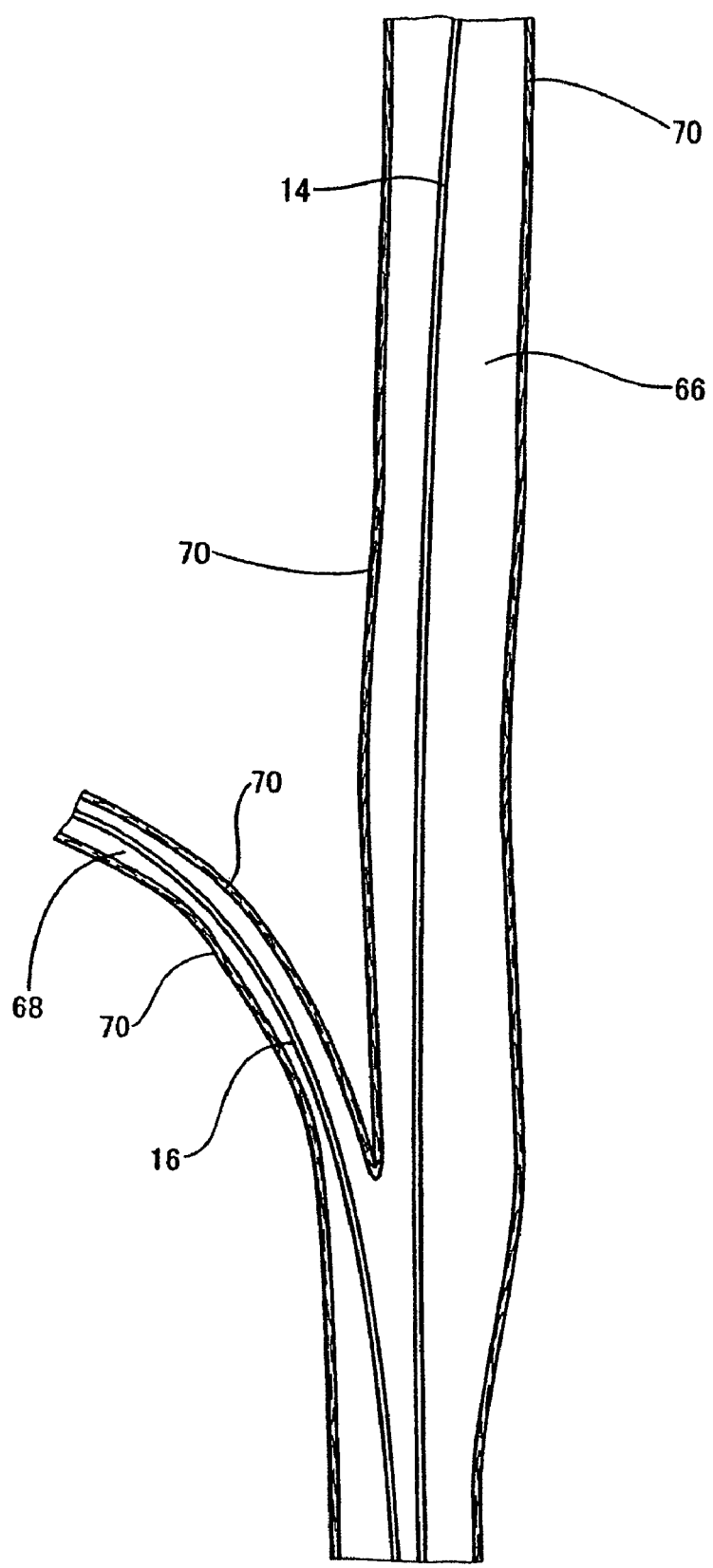
FIG. 11 is an explanatory drawing showing an embodiment of how the reagent injection device shown in FIG. 1 can be used to inject a specified reagent into a lesion in the cardiac muscle, with the first guide wire and second guide wire inserted into the main vessel and branch vessel, respectively, at the surface of the cardiac muscle.

Specifically, as shown in FIG. 11, in a reagent injection therapy using this reagent injection catheter, the first guide wire (14) is first inserted into a main vessel (66) at the surface of a cardiac muscle (64), for example.

Next, the rear end of the first guide wire (14) that will project outside the patient's body is inserted into the first guide wire lumen (26) through the first opening (28) in the main tube (10). It is then extended to the outside through the third opening (38) in the main tube (10). This way, the first guide wire (14) is inserted into the first guide wire lumen (26) in the main tube (10) in an axially movable manner.

Thereafter, the second guide wire (16) is inserted into the second guide wire lumen (34) through the second connection part (44) in the branching socket (40) provided at the rear end of the main tube (10). Then, the tip of this second guide wire (16) is passed through the second opening (36) and the support tube (60) (reinforcement tube (62)) and then extended to the outside of the main tube (10) through the opening provided at the tip of the support tube (60). This way, the second guide wire (16) is inserted into the second guide wire lumen (34) in the main tube (10), and also into the support tube (60), in an axially movable manner. At this time, the main tube (10) and support tube (60) are inserted through the first and second guide wires (14 and 16) over the cardiac muscle (64) in such a way that the projection aperture (32) is oriented toward the surface of the cardiac muscle (64). By the way, this insertion of the second guide wire (16) into the main tube (10) and support tube (60) and the above insertion of the first guide wire (14) into the main tube (10) are performed outside the patient's body.

Next, as shown in FIG. 11, the second guide wire (16) inserted into the main tube (10) and support tube (60) is inserted through the main vessel (66) into a branch vessel (68) that branches from the main vessel (66) at the surface of the cardiac muscle (64). This insertion of the second guide wire (16) into the main vessel (66) and branch vessel (68) and the aforementioned insertion of the first guide wire (14) into the main vessel (66) are generally performed manually.

Figure 12:
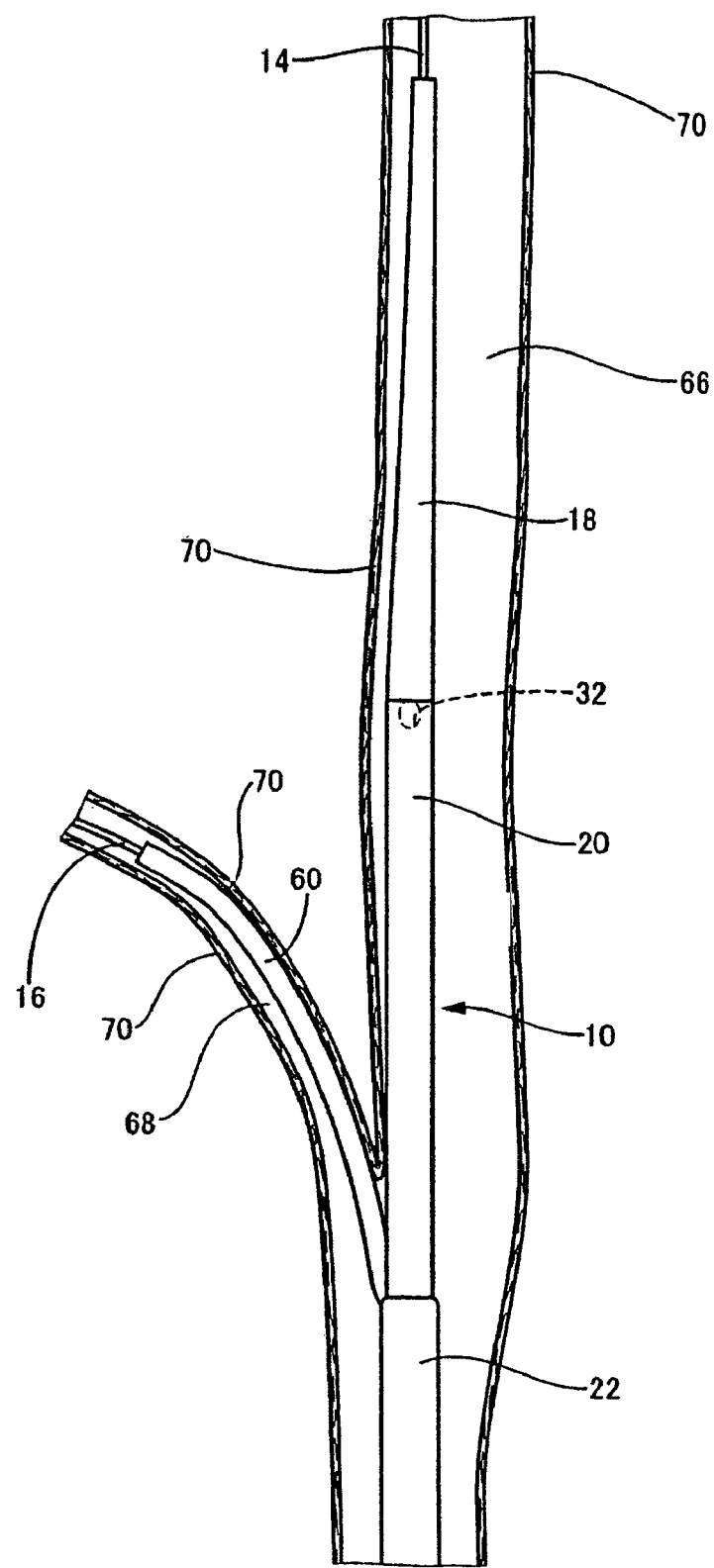
FIG. 12 is an explanatory drawing showing another embodiment of how the reagent injection device shown in FIG. 1 can be used to inject a specified reagent into a lesion in the cardiac muscle, with the main tube inserted into the main vessel along the first guide wire and second guide wire, and the support tube inserted into the branch vessel.

Thereafter, the main tube (10) is forwarded along the first guide wire (14) and second guide wire (16) and inserted into the main vessel (66). As shown in FIG. 12, the support tube (60) is then guided by the second guide wire (16) and the main tube (10) is moved forward through the main vessel (66) until the support tube (60) can be inserted into the branch vessel (68). At this time, insertion of the support tube (60) into the branch vessel (68) restores the circumferentially displaced main tube (10) back to the normal position that was set when the main tube (10) was first inserted. This way, the projection aperture (32) provided in the main tube (10) will be automatically positioned to open toward the surface of the cardiac muscle (64).

This operation is also performed while checking on a monitor, etc., via X-ray fluoroscopy the position of the main-body marker tube (56a) affixed near the projection aperture (32) in the main tube (10). In other words, the operation is deemed to have completed when the main-body marker tube (56a) is confirmed to have reached a specified location in the main vessel (66), with the support tube (60) inserted into the branch vessel (68), as explained above, following the insertion of the main tube (10) into the main vessel (66). This way, the projection aperture (32) can be positioned at a specified location in the main vessel (66) when the insertion of the main tube (10) into the main vessel (66) is completed.

As explained earlier, the main tube (10) is flexible. Additionally, the tip (18) of the main tube (10) is tapered to make the flexibility of this tip (18) higher than the flexibility of other parts. Furthermore, the base (24) that comprises a majority of the main tube (10) only has the needle-like tubular body lumen (30) and second guide wire lumen (34) inside, which makes it possible for the base (24) to have an oval cross-section shape having a cross-section area smaller than that of the first and second intermediate sections (20 and 22).

For this reason, the main tube (10) can be smoothly moved forward through the meandering main vessel (66) via this operation. During this forward movement, scratching of the inner surface of a vessel wall (70) of the main vessel (66) due to contact with the tip of the main tube (10) can be effectively avoided. Furthermore, a sufficient clearance is formed between the outer periphery surface of the main tube (10) and the inner surface of the vessel wall (70) of the main vessel (66). Therefore, the blood flow in the main vessel (66) into which the main tube (10) is inserted can be maintained favorably.

Moreover, in this case the tip of the support tube (60) is more flexible than the base part. The length of the support tube (60) is also set in such a way that it does not interfere with the insertion of the main tube (10) into the main vessel (66). Therefore, when this support tube (60) is inserted into the main vessel (66) together with the main tube (10), or when the support tube (60) is inserted into the branch vessel (68), scratching of the inner surface of the main vessel (66) or branch vessel (68) can be favorably avoided. Furthermore, the outer diameter of the support tube (60) is reduced to a very small size equivalent to the small-diameter end of the tip (18) of the main tube (10). Therefore, insertion of the support tube (60) will not inhibit the blood flow in the branch vessel (68).

Next, the needle-like tubular body (12) is inserted into the needle-like tubular body lumen (30) in the main tube (10) through the first connection part (42) in the branching socket (40), and then moved forward in the insertion direction of the main tube (10) into the main vessel (66).

Figure 13:
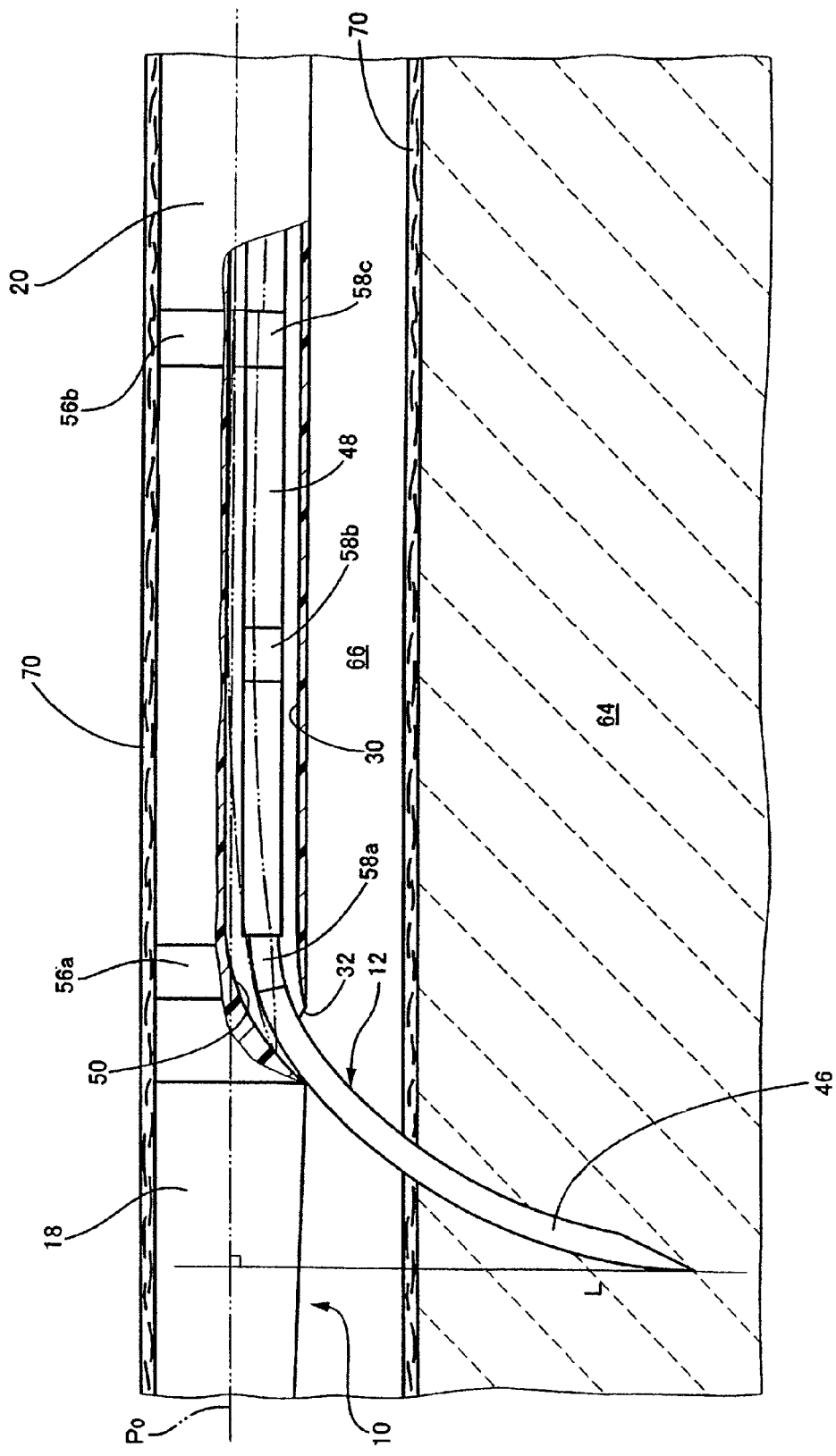
FIG. 13 is an explanatory drawing showing yet another embodiment of how the reagent injection device shown in FIG. 1 can be used to inject a specified reagent into a lesion in the cardiac muscle, with the needle puncturing the cardiac muscle.

At this time, as indicated by the two-dot chain line in FIG. 13, once reaching the front end of the needle-like tubular body lumen (30) the needle (46) at the tip of the needle-like tubular body (12) is caused to slide along the guide surface (50) provided on the inner periphery at the front end of the needle-like tubular body lumen (30), thereby smoothly moving forward toward the projection aperture (32). When this needle-like tubular body (12) is further moved forward, the needle (46) projects out of the projection aperture (32), as indicated by the solid line in FIG. 13.

Therefore, this operation allows the needle (46) of the needle-like tubular body (12) projecting out of the projection aperture (32) in the main tube (10) to pierce through the vessel wall (70) of the main vessel (66) and puncture a specified location in the target lesion in the cardiac muscle (64). By the way, this operation of projecting the needle (46) and puncturing the cardiac muscle via the movement of the needle-like tubular body (12) is performed manually or using a known screw mechanism, etc.

This puncturing of the cardiac muscle (64) by the needle (46) is also performed under X-ray fluoroscopy in the same manner as when the main tube (10) is inserted into the main vessel (66). In other words, this operation allows the needle-like tubular body (12) to be moved through the main tube (10) while checking via X-ray fluoroscopy the relative positions of the three needle marker tubes (58a, 58b and 58c) affixed onto the needle-like tubular body (12) with respect to the main-body second marker tube (56b).

In this operation, as explained earlier whether the tip of the needle (46) has reached the position of the projection aperture (32) can be easily identified by checking the relative position of the needle first marker tube (58a) with respect to the main-body second marker tube (56b). Also, the projected length of the needle-like tubular body (12) from the projection aperture (32) can be easily identified by checking the relative positions of the needle second marker tube (58b) and needle third marker tube (58c) with respect to the main-body second marker tube (56b) before the needle-like tubular body (12) is moved further forward when the tip of the needle (46) has reached the projection aperture (32). Also, thus identified position of the needle-like tubular body (12) inside the main tube (10) and its projected length from the projection aperture (32) can be used as guidelines to identify the punctured depth of the cardiac muscle (64) by the needle (46).

As explained earlier, in this embodiment the needle (46) of the needle-like tubular body (12) can be projected out of the projection aperture (32) in the direction virtually perpendicular to the extension directions of the first guide wire (14) and second guide wire (16) from the main tube (10), when the first guide wire (14) and second guide wire (16) are respectively inserted into the main vessel (66) and branch vessel (68) traveling at the surface of the cardiac muscle (64). This needle (46) then punctures the cardiac muscle (64).

Figure 10:
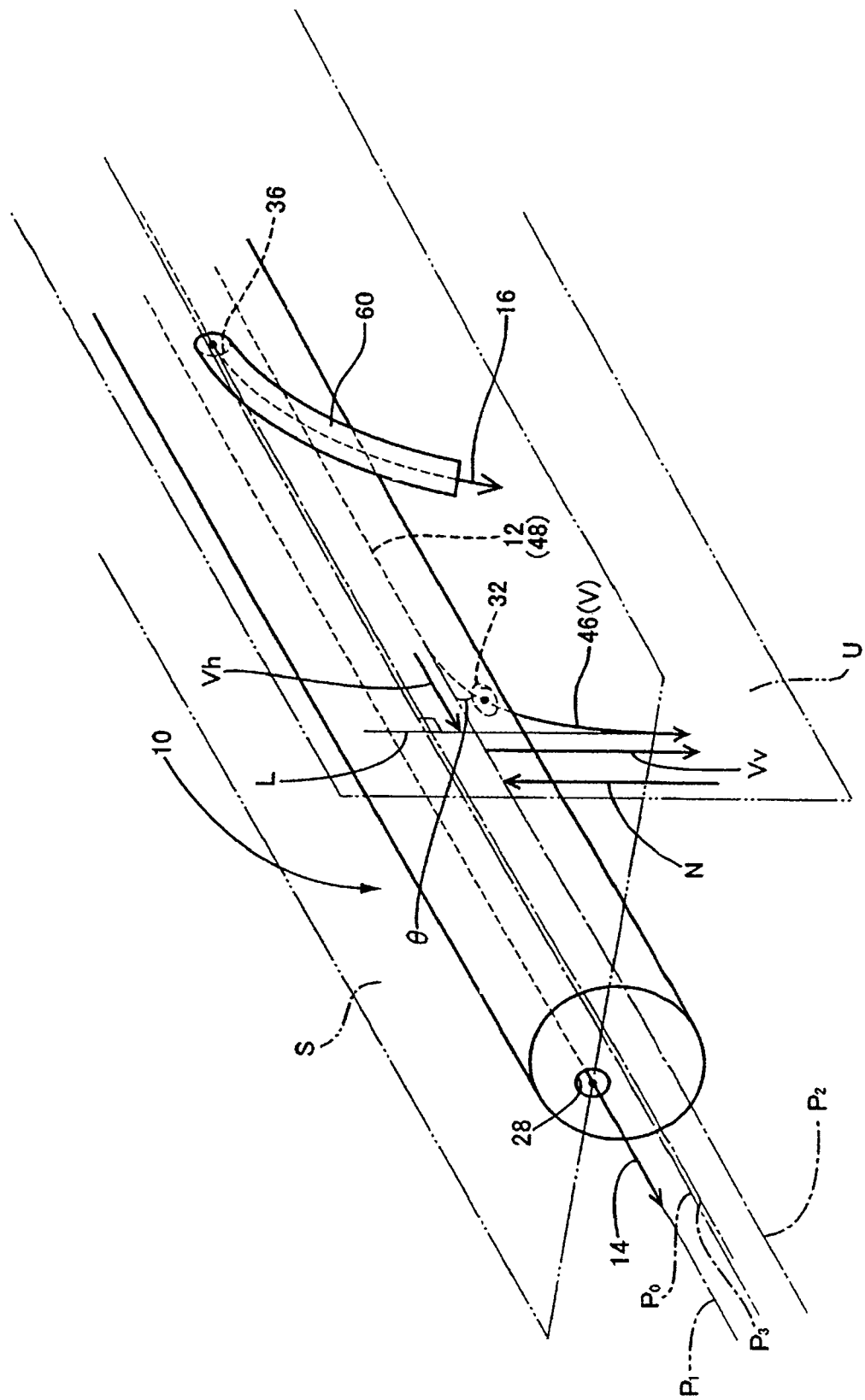
FIG. 10 is an explanatory drawing showing a schematic layout of the needle-like tubular body, first guide wire and second guide wire inserted into the main tube of the reagent injection device shown in FIG. 1.

Therefore, as shown in FIG. 10, plane S formed by the first guide wire (14) and second guide wire (16) virtually indicates the surface of the cardiac muscle (64). Vector V formed in the moving direction of the needle (46) of the needle-like tubular body (12) into the cardiac muscle (64), and the needle-like tubular body (12) and the center axis ($P_0$) of the second intermediate section (20) of the main tube (10), form another plane U crossing at right angles with plane S. Furthermore, this vector V is divided into Vv perpendicular to plane S, and Vh extending forward along the center axis ($P_0$) of the first intermediate section.

On the other hand, reactive force N (puncturing reactive force) that acts upon the main tube (10) via the needle (46) in the direction opposite to the moving direction of the needle (46) when the needle (46) enters the cardiac muscle (64) is roughly the same in magnitude as the aforementioned vector Vv acting perpendicularly to plane S but is exerted in the opposite direction.

Therefore, puncturing reactive force N that generates when the needle (46) enters the cardiac muscle (64) can be divided into two components and received by the first guide wire (14) and second guide wire (16) inside plane S formed by the two guide wires (14 and 16).

Also, these first guide wire (14) and second guide wire (16) are positioned in such a way that the two extend in parallel and side by side in the lateral direction through the second intermediate section (22) of the main tube (60) before the position at which the second guide wire (16) extends to the outside of the main tube (10) through the support tube (60). Therefore, the aforementioned puncturing reactive force N can be received in a more stable manner within plane S formed by the first guide wire (14) and second guide wire (16).

In addition, this operation allows the support tube (60) to be inserted into the branch vessel (68), in addition to the first guide wire (14) and second guide wire (16) that are inserted into the main vessel (66) and branch vessel (68), respectively. Because of this, puncturing reactive force N generated when the needle (46) enters the cardiac muscle (64) is reliably received not only by the first guide wire (14) and second guide wire (16), but also by the support tube (60).

Therefore, compared with when only the first guide wire (14) and second guide wire (16) are inserted into the main vessel (66) and branch vessel (68), respectively, rotation of the main tube (10) about its axis center in the main vessel (66) due to the aforementioned puncturing reactive force can be prevented in a more favorable manner.

In addition, the movement of the needle-like tubular body (12) can be terminated once the needle (46), thus pierced into the target lesion in the cardiac muscle (64), has reached a specified depth at the lesion. Thereafter, a reagent containing a cell or growth factor formulated to regenerate the cardiac muscle (64) is introduced into the inner hole inside the needle-like tubular body (12) through a syringe (54) connected to the connector (52) at the rear end of the needle-like tubular body (12). Then, the reagent is discharged to the outside through the opening at the tip of the needle (46) and injected into the lesion in the cardiac muscle (64).

Once the reagent has been injected in one lesion in the cardiac muscle (64), successively the needle-like tubular body (12) is pulled back inside the main tube (10) and the needle (46) is retracted into the main tube (10). Thereafter, this reagent injection operation is repeated multiple times at different locations in the cardiac muscle (64). This way, the reagent will be injected into multiple lesions in the cardiac muscle (64).

As explained above, even without a balloon or other device normally installed on conventional catheters, the reagent injection catheter provided in this embodiment can cause the needle (46) to safely puncture the cardiac muscle (64) in a manner inhibiting the rotation of the main tube (10) due to the puncturing reactive force when the main tube (10) is inserted into a specified position in the main vessel (66).

Therefore, this embodiment allows the needle (46) to puncture, to a desired depth, the target lesion at a specified location in the cardiac muscle (64) in a smoother and more reliable manner, while at the same time realizing a smaller diameter or size by reason of elimination of the balloon. As a result, a reagent can be injected in a easier, safer and more accurate manner in a specified location of the cardiac muscle (64).

Also, the reagent injection catheter provided in this embodiment has a tapered tip (18) of the main tube (10), while the base (24) has a overall cross-section shape with a small cross-section area. Furthermore, the tip of the support tube (60) integrally formed with the main tube (10) is more flexible than the base part. Moreover, the overall length of this support tube (60) is set in such a way that, while maintaining its flexibility, the support tube (60) does not interfere with the insertion of the main tube (10) into the main vessel (66).

Therefore, this embodiment allows the main tube (10) and support tube (60) to be moved smoothly inside the main vessel (66) and branch vessel (68). Also, the inner surfaces of the main vessel (66) and branch vessel (68) are prevented from being scratched during the movements of the tubes (10 and 60). Furthermore, the blood flows in the main vessel (66) and branch vessel (68) can be maintained sufficiently.

Therefore, using the reagent injection catheter provided in this embodiment will ensure an extremely smooth and safe insertion of reagents into lesions in the cardiac muscle (64).

Additionally, the reagent injection catheter provided in this embodiment utilizes the main-body maker tubes (56) and needle marker tubes (58), which are affixed onto the main tube (10) and needle-like tubular body (12), respectively, to allow for easy identification of the position of the needle (46) of the needle-like tubular body (12) inside the main tube (10) that has been inserted into the main vessel (66), and also of the punctured depth of the cardiac muscle (64) by the needle (46).

Therefore, using this reagent injection catheter the punctured depth and puncturing speed of the cardiac muscle (64) by the needle (46) can be adjusted in an extremely easy and appropriate manner in accordance with the position of the needle-like tubular body (12) inside the main tube (10), punctured depth of the cardiac muscle (64) by the needle (46), and so on. As a result, the reagent can be injected more accurately and appropriately into lesions and other areas of the cardiac muscle (64).

Figure 14:
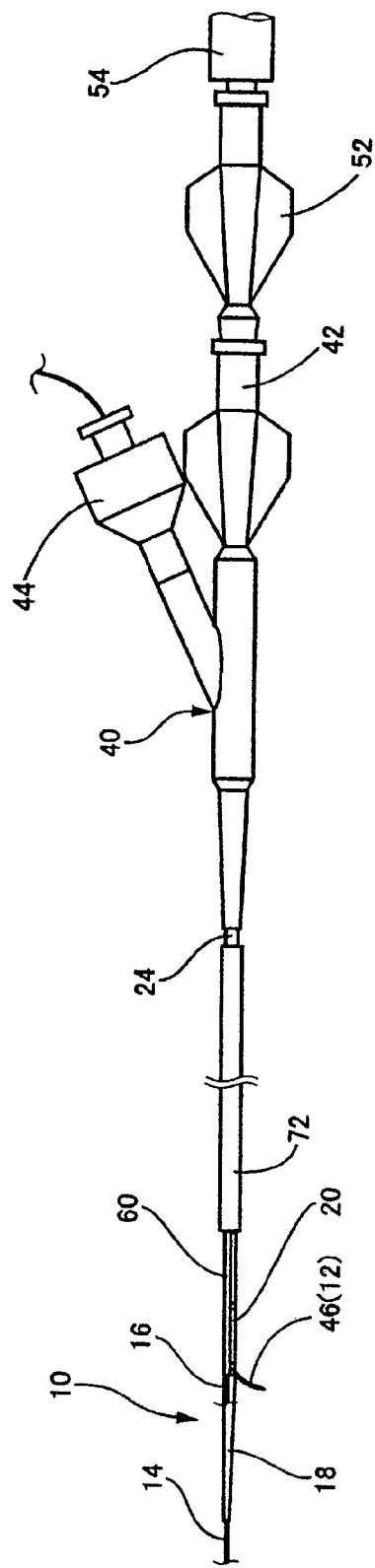
FIG. 14 is a drawing corresponding to FIG. 1, showing another embodiment of a reagent injection device conforming to the present invention.
Figure 15:
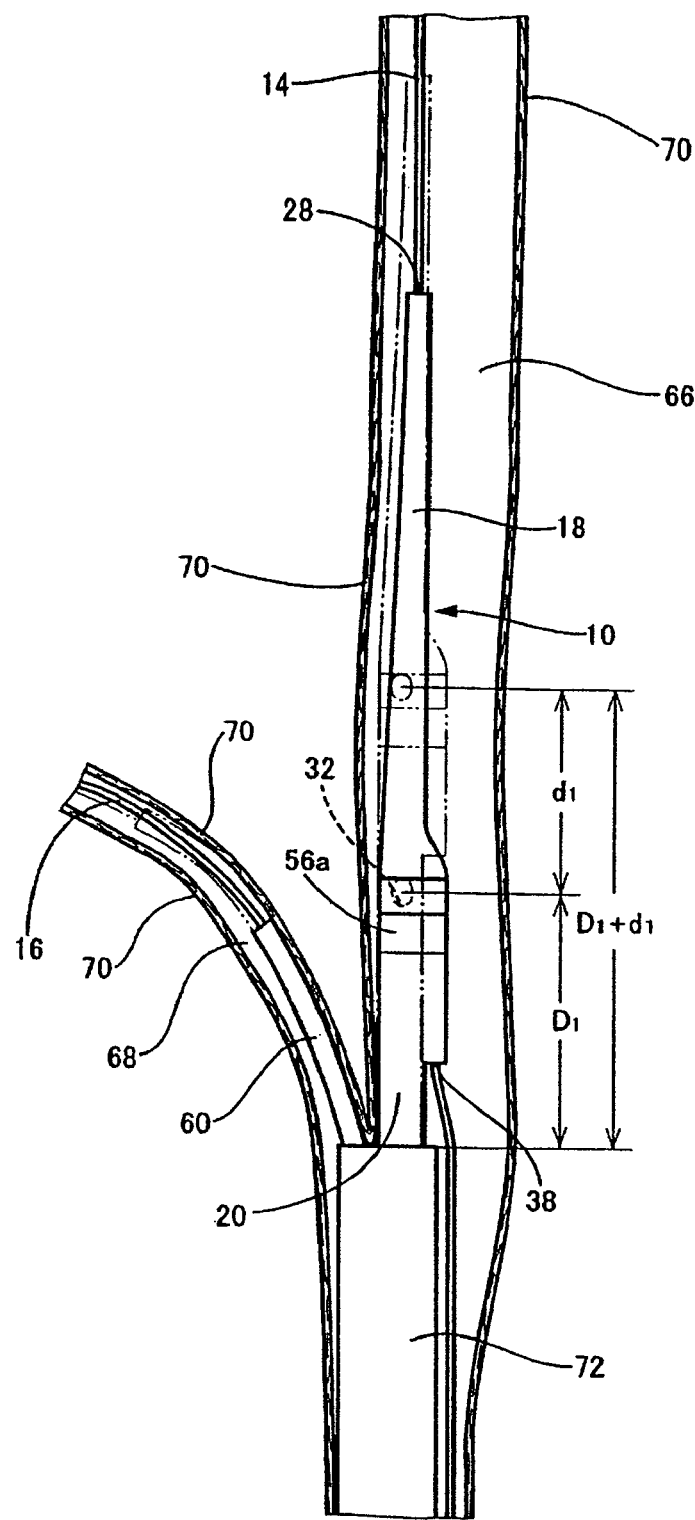
FIG. 15 is an explanatory drawing corresponding to FIG. 12, showing an embodiment of how the reagent injection device shown in FIG. 14 can be used to inject a specified reagent into a lesion in the cardiac muscle.

Next, FIGS. 14 and 15 illustrate another embodiment in which a cover tube provided as an external member is placed over the main tube. The two embodiments—one is illustrated by FIGS. 14 and 15 and the other by FIGS. 16 through 21 to be presented later on—are not explained in details, but they are referenced using the same symbols shown in FIGS. 1 through 13 corresponding to the respective parts of the structure explained in the aforementioned first embodiment.

Specifically, the reagent injection catheter provided in this embodiment has a cover tube (72) placed over a main tube (10) in an axially movable manner, as evident from FIG. 14. This cover tube (72) is formed using the same material as the main tube (10), for example, and has sufficient flexibility. Also, its overall length is roughly the same as the length of the section from the rear end of a base (24) to the rear end of a first intermediate section (20). Also, by allowing this cover tube (72) to move forward relative to the main tube (10), the first intermediate section (20) of the main tube (10), and a support tube (60), can be covered and restrained by the cover tube (72) (refer to FIG. 15).

Therefore, in this case the cover tube (72) is placed over the main tube (10) and moved forward relative to the main tube (10) to achieve a condition where the side of the rear end of the first intermediate section (20) as well as the side of the rear end of the support tube (60) are restrained by the tip of the cover tube (72). This way, of the overall length of the support tube (60), the length of the section not covered by the cover tube (72) can be shortened in accordance with a given forward movement of the cover tube (72) relative to the main tube (10). Also, the distance from the front end of the cover tube (72) to a projection aperture (32) in the main tube (10) can also be reduced in accordance with a given forward movement of the cover tube (72) relative to the main tube (10).

On the other hand, moving the cover tube (72) backward relative to the main tube (10) will increase the length of the tip section of the support tube (60) not covered by the cover tube (72), and also the distance from the front end of the cover tube (72) to a projection aperture (32) in the main tube (10), in accordance with a given backward movement of the cover tube (72) relative to the main tube (10).

In other words, the branching location of the support tube (60) from the main tube (10) can be substantially shifted forward in accordance with the placement position of the cover tube (72) over the main tube (10), which effectively adjusts the length of the section, of the overall support tube (60), where flexible deflection and deformation is allowed. Also, the distance from the front end of the cover tube (72) to the projection aperture (32) in the main tube (10) can be adjusted in accordance with the placement position of the cover tube (72) over the main tube (10).

By the way, in this embodiment a third opening (38) is provided in the tube wall of the first intermediate section (20) of the main tube (10), at a position corresponding to about a half length of the support tube (60). Also, a first guide wire (14) is extending out of the main tube (10) through the third opening (38). For this reason, further forward movement of the cover tube (72) will be restricted by contact between the front end of the cover tube (72) and the part of the first guide wire (14) extending from the third opening (38). This way, coverage of the entire support tube (60) by the cover tube (72) can be prevented when the cover tube (72) is unduly moved forward relative to the main tube (10), while at the same time blocking of the projection aperture (32) by the cover tube (72) can also be prevented. In addition, the part of the cover tube (72) covering the rear end of the base (24) of the main tube (10) will still project outside the patient's body together with the rear end of the base (24), even when the cover tube (72) is at the aforementioned forward movement limit position.

Therefore, when inserting a specified reagent into a cardiac muscle (64) using a reagent injection catheter having such cover tube (72), the first step is to insert the first guide wire (14) and a second guide wire (16) into a main vessel (66) and a branch vessel (68), respectively, just like in the aforementioned embodiment.

Thereafter, the cover tube (72) is moved forward by a specified distance relative to the main tube (10), for example, until the front end of the support tube (60) not covered by the cover tube (72) is shortened by a desired length, and in this condition the main tube (10) and cover tube (72) are inserted into the main vessel (66) along the first guide wire (14), as shown in FIG. 15. Then, the cover tube (72) and main tube (10) are moved forward through the main vessel (66) up to a position where the front end of the cover tube (72) contacts, via the support tube (60), the branching location of the main vessel (66) and branch vessel (68).

This way, only the tip part of the overall support tube (60), which is not covered by the cover tube (72) and where flexible deflection and deformation is allowed, is inserted into the branch vessel (68) along the second guide wire (16). Also, the projection aperture (32) in the main tube (10) is positioned a specified distance ($D_1$) away from the front end of the cover tube (72) in the main vessel (66).

Next, in the same way as in the aforementioned embodiment a needle-like tubular body (12) is inserted into the main tube (10) and moved forward. Then, a needle (46) of the needle-like tubular body (12) is projected out of the projection aperture (32) and pierced into the cardiac muscle (64) to a specified depth. At this time, the needle (46) punctures the cardiac muscle (64) at a position a specified distance ($D_1$) away from the position corresponding to the front end of the cover tube (72).

Thereafter, a specified reagent is supplied into the needle-like tubular body (12) through a syringe (54), and the reagent is injected through the needle (46) into the cardiac muscle

(64) at a location a specified distance (D₁) away from the location corresponding to the front end of the cover tube (72).

To repeat this reagent injection operation in a different location of the cardiac muscle (64) after the initial reagent injection operation has completed, the needle (46) is retracted into the main tube (10), after which the section of the cover tube (72) exposed outside the patient's body is handled so that the cover tube (72) position is secured in place. Next, the main tube (10) is operated from outside the patient's body to achieve a forward movement relative to the cover tube (72) by a specified distance (d₁). At this time, the length of the tip section of the support tube (60) not covered by the cover tube (72) and the distance from the front end of the cover tube (72) to the projection aperture (32) are increased by the distance of this relative movement (d₁) effected by the relative forward movement of the main tube (10).

This way, the support tube (60) is inserted into the branch vessel (68) by a length longer than the inserted length of the support tube (60) into the branch vessel (68) in the initial reagent injection operation, as indicated by the two-dot chain line in FIG. 15. Also, the projection aperture (32) in the main tube (10) is positioned in the main vessel (66) $D_1+d_1$ away from the front end of the cover tube (72).

Next, the needle-like tubular body (12) of the main tube (10) is moved forward and the needle (46) is projected out of the projection aperture (32). This way, the needle (46) can puncture the cardiac muscle (64) to a specified depth at a location $D_1+d_1$ away from the location corresponding to the front end of the cover tube (72). Thereafter, the reagent supplied from the syringe (54) is injected through the needle (46) into the location of the cardiac muscle (64) punctured by the needle (46). Of course, the cover tube (72) can be moved relative to the main tube (10) in this operation.

As explained above, in this embodiment the cardiac muscle (64) can also be punctured in a condition where the first guide wire (14) is inserted into the main vessel (66), while the second guide wire (16) and the support tube (60) supporting the second guide wire are inserted into the branch vessel (68). Therefore, the excellent action and effect obtained in the aforementioned first embodiment can be received in an extremely favorable manner.

In particular, this embodiment allows the position of the projection aperture (32) to be changed at will inside the main vessel (66), by relative movement of the main tube (10) and cover tube (72) by a specified distance. This allows the needle (46) to puncture multiple desired locations in the cardiac muscle (64). Also, the cover tube (72) effectively aligns the position at which the support tube (60) branches from the main tube (10), with the position at which the branch vessel (68) branches from the main vessel (66). For this reason, displacement (rotation) of the main tube (10) about its longitudinal axis can be effectively prevented. This, in turn, stabilizes the operation of the reagent injection catheter.

Therefore, using the reagent injection catheter provided in this embodiment allows for accurate injection of a reagent into multiple specified locations in the cardiac muscle (64).

Furthermore, this reagent injection catheter allows the cover tube (72) and main tube (10) to be operated from outside the patient's body to achieve relative movements. This achieves easier and smoother reagent injection operations at multiple desired locations in the cardiac muscle (64).

Additionally, this embodiment provides a third opening (38) forward of the location where a second opening (36) is formed in the first intermediate section (20). As a result, only the second guide wire lumen (34) and needle-like tubular body lumen (30) are provided inside the second intermediate section (22), without the first guide wire lumen (26). For this reason, the second intermediate section (22) can be made thinner than when the first guide wire lumen (26), second guide wire lumen (34) and needle-like tubular body lumen (30) are all provided inside the second intermediate section (22). In this sense, this embodiment provides the advantage of being able to reduce the diameter of the main tube (10) in a more favorable manner.

Figure 16:
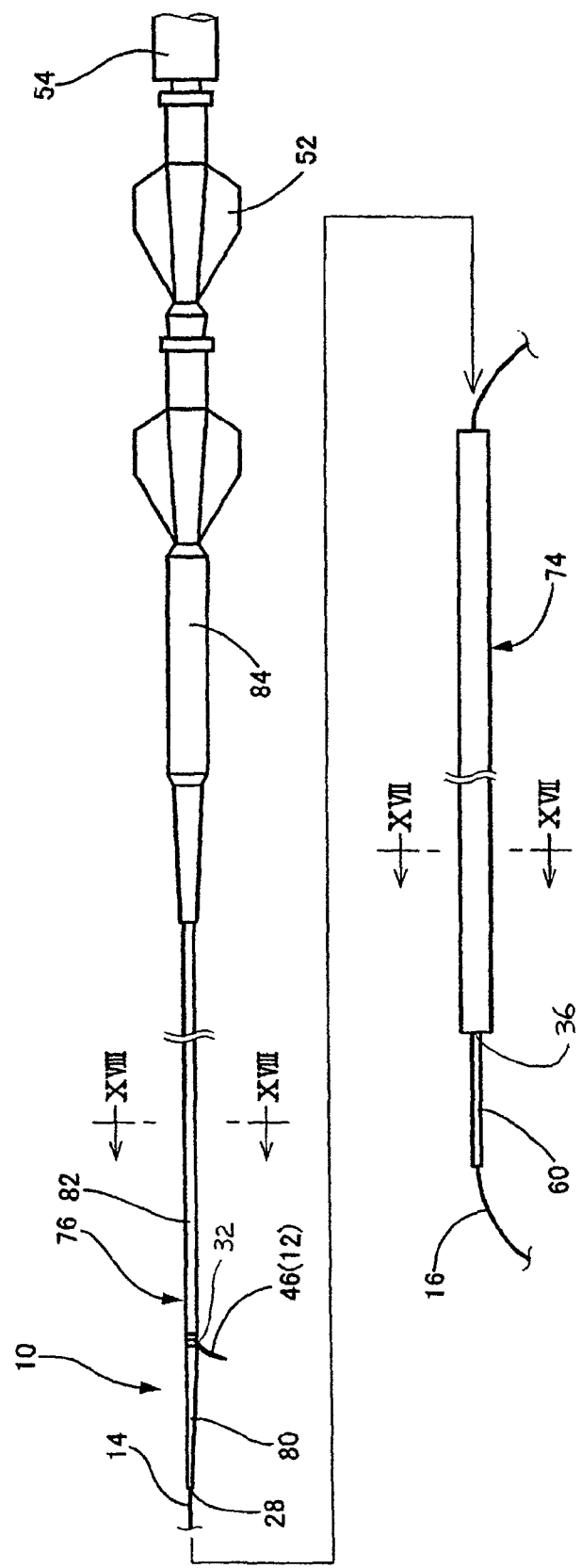
FIG. 16 is a drawing explaining yet another embodiment of a reagent injection device conforming to the present invention, illustrating a dissembled state of the main tube.

Next, FIG. 16 illustrates yet another embodiment, in which the main tube has a dual-tube structure different from the structure presented in the aforementioned first and second embodiments.

In other words, the reagent injection catheter in this embodiment has a main tube (10) comprising an outer tube (74) and an inner tube (76), as evident from FIG. 16. Then, these outer tube (74) and inner tube (76) are formed using a material similar to what is used to form the main tube (10) in the aforementioned first and second embodiments. This way, each tube is given sufficient flexibility.

Figure 17:
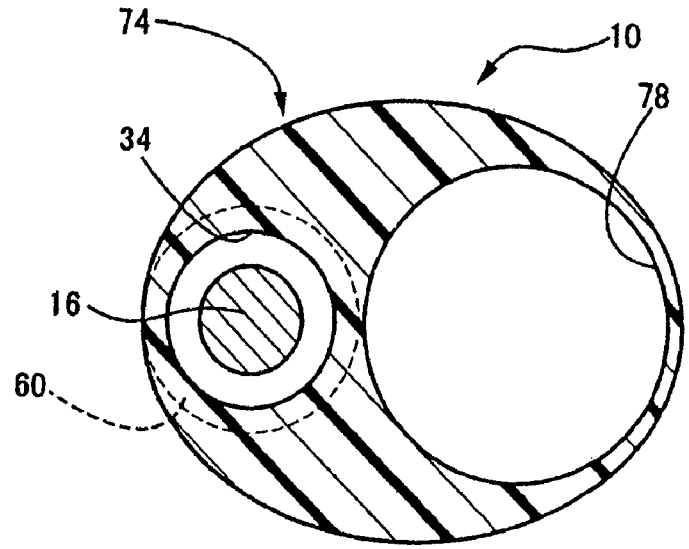
FIG. 17 is an explanatory drawing showing an enlarged XVII-XVII section view of FIG. 16.
Figure 18:
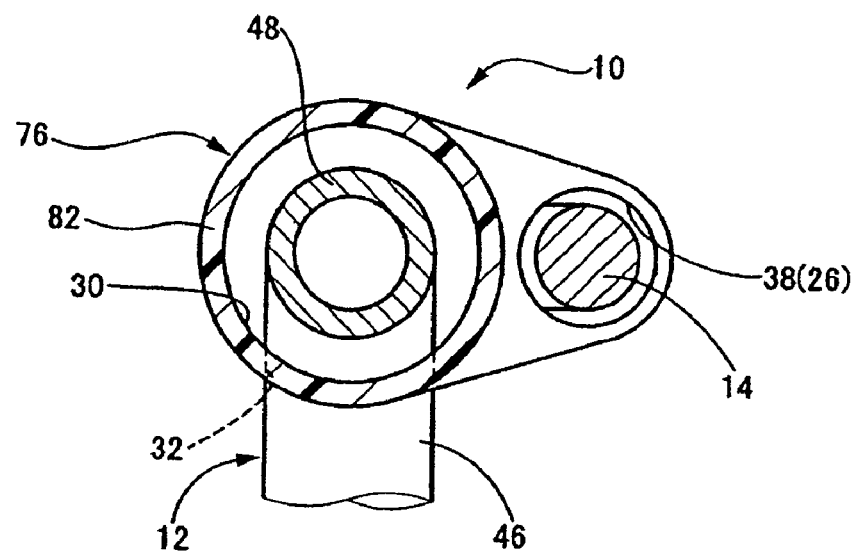
FIG. 18 is an explanatory drawing showing an enlarged XVIII-XVIII section view of FIG. 16.

In addition, as shown in FIGS. 16 through 18 the outer tube (74) comprises a long tubular body having an oval cross-section shape. In this outer tube (74), a second guide wire lumen (34) and an inner hole (78) having a cylindrical inner periphery surface are formed side by side in parallel in a manner extending continuously in the axial direction. The second guide wire lumen (34) and inner hole (78) also open at the front (left in FIG. 16) and rear (right in FIG. 16) of the outer tube (74), respectively. In other words, in this structure the front opening of the second guide wire lumen (34) provided in the front end of this outer tube (74) forms a second opening (36). Then, a support tube (60) having a specified length is formed integral with the front end face of this outer tube (74) in such a way that it connects to the second opening (36) and extends straight forward.

On the other hand, the inner tube (76) comprises a tip section (80) and a base section (82) positioned in this order from the front side. The base section (82) provides a cylindrical outer periphery surface that can slide against the inner periphery surface of the inner hole (78) in the outer tube (74) in both the axial direction and circumferential direction. Also, a needle-like tubular body lumen (30) is formed inside this base section (82) in a manner extending continuously in the axial direction. On the other hand, a first guide wire lumen (26) is formed inside the tip section (80) in a manner extending continuously in the axial direction. Note that a third opening (38) is formed to the rear of a projection aperture (32) provided in the tube wall of the tip section (80).

A needle-like tubular body (12) is then inserted into this needle-like tubular body lumen (30), through a socket (84) connected to the base section (82), in an axially movable manner. Also, a needle (46) of this needle-like tubular body (12) can project downward through the projection aperture (32) provided in the tube wall of the tip section (80). On the other hand, a first guide wire (14) is inserted into the first guide wire lumen (26) in an axially movable manner. Also, this first guide wire (14) is extended forward and rearward through a first opening (28) provided in the tip section (80) and the third opening (38), respectively.

Here, this inner tube (76) is inserted, at its base section (82), into the inner hole (78) of the outer tube (74) movably in both the circumferential direction and axial direction, thereby comprising the main tube (10). Accordingly, the support tube (60) is integrally provided on this main tube (10) in a position where the support tube (60) extends in parallel with the tip section (80) of the inner tube (76).

Also, the reagent injection catheter provided in this embodiment allows the installation position of the support tube (60) to be changed in the axial direction by relative movement of the inner tube (76) and outer tube (74) in the axial direction. At the same time, the distance from the front end of the outer tube (74) to the projection aperture (32) in the inner tube (76) can also be changed. Furthermore, the position of the support tube (60) relative to the inner tube (76) in the circumferential direction can be changed by relative movement of the inner tube (76) and outer tube (74) in the circumferential direction.

Therefore, to inject a specified reagent into a cardiac muscle (64) using a reagent injection catheter having such structure, the first step is to insert the first guide wire (14) and a second guide wire (16) into a main vessel (66) and a branch vessel (68), respectively, in the same manner as in the aforementioned first and second embodiments.

Figure 19:
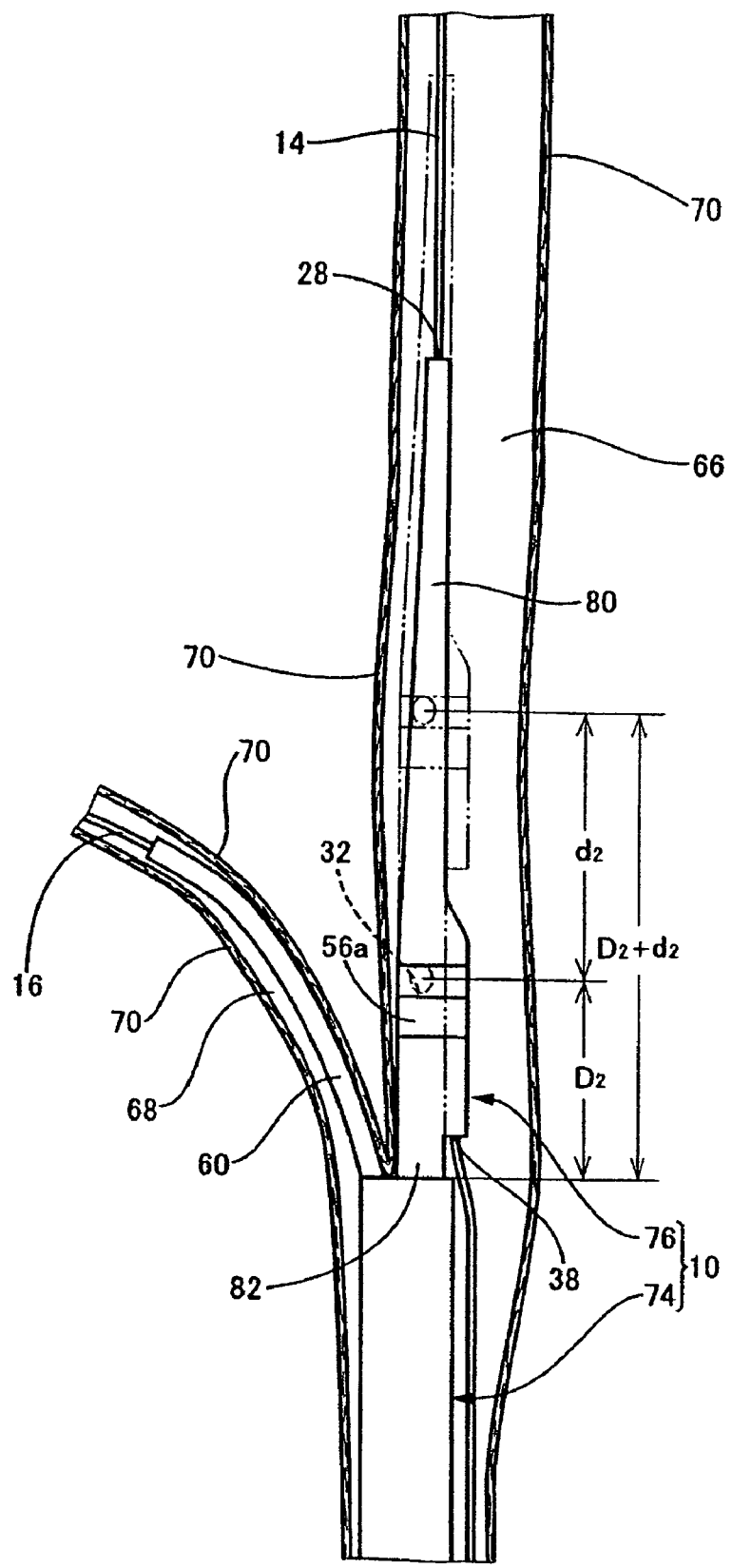
FIG. 19 is an explanatory drawing corresponding to FIG. 12, showing an embodiment of how the reagent injection device shown in FIG. 16 can be used to inject a specified reagent into a lesion in the cardiac muscle.

Thereafter, for example, the main tube (10) comprising the inner tube (76) inserted into the outer tube (74), in a manner achieving a relatively short distance ($D_2$) between the front end of the outer tube (74) and the projection aperture (32) in the inner tube (76), is inserted into the main vessel (66) along the first guide wire (14) and a second guide wire (16), as shown in FIG. 19. Then, the main tube (10) is moved forward in the main vessel (66) until the front end of the outer tube (76) reaches the position at which it contacts the branching location of the main vessel (66) and branch vessel (68). At this time, both the rear end of the outer tube (74) and the rear end of the inner tube (76) are exposed outside the patient's body.

Next, the needle-like tubular body (12) is inserted into the inner tube (76) of the main tube (10) and moved forward. Then, the needle (46) of the needle-like tubular body (12) is projected out of the projection aperture (32) and pierced into the cardiac muscle (64) to a specified depth. At this time, the needle (46) punctures the cardiac muscle (64) at a position a specified distance ($D_2$) away from the position corresponding to the front end of the outer tube (74).

Thereafter, a specified reagent is supplied into the needle-like tubular body (12) through a syringe (54) and the reagent is injected into the cardiac muscle (64) through the needle (46) at a location a specified distance ($D_2$) away from the location corresponding to the front end of the outer tube (74).

To repeat this reagent injection operation in a different location of the cardiac muscle (64) after the initial reagent injection operation has completed, the needle (46) is retracted into the main tube (10), after which the section of the outer tube (74) exposed outside the patient's body is handled and the entire inner tube (76) is operated from outside the patient's body to achieve a forward movement relative to the outer tube (74) by a specified distance ($d_2$).

At this time, the inserted length of the support tube (60) into the branch vessel (68) does not change at all, while the distance from the front end of the outer tube (74) to the projection aperture (32) is increased by the distance of relative forward movement ($d_2$) of the inner tube (76). This way, the projection aperture (32) in the inner tube (76) is positioned $D_2+d_2$ away from the front end of the outer tube (74) inside the main vessel (66).

Next, the needle-like tubular body (12) in the main tube (10) is moved forward and the needle (46) is projected out of the projection aperture (32). As a result, the needle (46) punctures the cardiac muscle (64) to a specified depth at a location a specified distance ($D_2+d_2$) away from the location corresponding to the front end of the outer tube (74) over the cardiac muscle (64). Thereafter, the reagent supplied from the syringe (54) is injected through the needle (46) into the location of the cardiac muscle (64). Of course, the outer tube (74) can be moved relative to the inner tube (76) in this operation.

As explained above, in this embodiment the cardiac muscle (64) can also be punctured in a condition where the first guide wire (14) is inserted into the main vessel (66), while the second guide wire (16) and the support tube (60) supporting the second guide wire (16) are inserted into the branch vessel (68). Therefore, the excellent action and effect obtained in the aforementioned first embodiment can be received in an extremely favorable manner.

In particular, this embodiment allows the position of the projection aperture (32) to be changed at will inside the main vessel (66), by relative movement of the outer tube (74) and inner tube (76), together comprising the main tube (10), by a specified distance. Also, this allows the needle (46) to puncture multiple desired locations in the cardiac muscle (64).

Additionally, the inserted length of the support tube (60) into the branch vessel (68) does not change at all, even if the position of the projection aperture (32) changes inside the main vessel (66) due to relative axial movement of the outer tube (74) and inner tube (76). Therefore, change in the ability of the support tube (60) to support the Aforementioned puncturing reactive force can be favorably avoided.

Therefore, use of the reagent injection catheter provided in this embodiment allows for accurate injection of a reagent into multiple specified locations in the cardiac muscle (64). Furthermore, this reagent injection catheter can achieve more stable and smoother reagent injection operations at multiple desired locations in the cardiac muscle (64).

In addition, in this embodiment the inner tube (76) and outer tube (74) are able to move relatively in the circumferential direction, and this relative circumferential movement allows the support tube (60) to move relative to the projection aperture (32). Therefore, even if the branch vessel (68) is displaced with respect to the main vessel (66) or branched from the main vessel to either left or right, the second guide wire (16) and support tube (60) can be reliably inserted into the branch vessel (68) while maintaining the opening direction of the projection aperture (32), or the projecting direction of the needle (46).

Therefore, the reagent injection catheter provided in this embodiment can achieve a smoother and easier reagent injection operation with respect to the cardiac muscle (64).

In addition, this reagent injection catheter allows the inner tube (76) and outer tube (74) to be operated from outside the patient's body to achieve relative movements. Therefore, it has the advantage of enabling easier and smoother reagent injection operations at multiple desired locations in the cardiac muscle (64).

Furthermore, in this embodiment the outer tube (74) comprising the outer part of the main tube (10) comprises a tubular body having an oval cross-section shape. Therefore, a clearance is formed between the outer periphery surface of the outer tube (74) and the inner periphery surface of the main vessel (66) when the main tube (10) is inserted into the main vessel (66), thereby maintaining the blood flow.

Therefore, the reagent injection catheter provided in this embodiment can effectively ensure safety of reagent injection operation with respect to the cardiac muscle (64).

The forgoing described the specific structures of the present invention in details. Note, however, that these are only embodiments and the present invention is not limited in any way by the descriptions given above.

For example, the outer periphery surface or exterior shape of the main tube (10) is not at all limited to the shapes given in the embodiments.

Also, in the aforementioned first embodiment the main tube (10) is formed by integrally bonding four tubes that respectively comprise the tip (18), first intermediate section (20), second intermediate section (22) and base (24). However, the main tube (10) having such four sections can also be formed by integral forming such as extrusion using a specified resin material.

Additionally, the forming positions of the first opening (28), second opening (36), third opening (38) and projection aperture (32) are not specifically limited to the positions indicated in the aforementioned three embodiments.

For example, in the first embodiment it is also possible to provide the third opening (38) in the first intermediate section (20) that only has the first guide wire lumen (26) and needle-like tubular body lumen (30). This way, the second intermediate section (22) having the first guide wire lumen (26), needle-like tubular body lumen (30) and second guide wire lumen (34) can be omitted. This further reduces the diameter of the main tube (10) in a favorable manner.

In addition, in all of the aforementioned three embodiments the reinforcement tube (62) is inserted into the support tube (60) at its base, thereby making the tip of the support tube (60) more flexible than the base part where the reinforcement tube (62) is inserted. However, the structure that enhances the flexibility of the tip of the support tube (60) is not limited to the one just mentioned. For example, the tip of the support tube (60) can be made thinner than the base part, or the tip can be formed using a material more flexible than the material for the base part, thereby making the tip of the support tube (60) more flexible than the base part.

It also goes without saying that the numbers and positions of the main-body marker tubes (56) and needle marker tubes (58) are not specifically limited to those in the embodiments.

Figure 20:
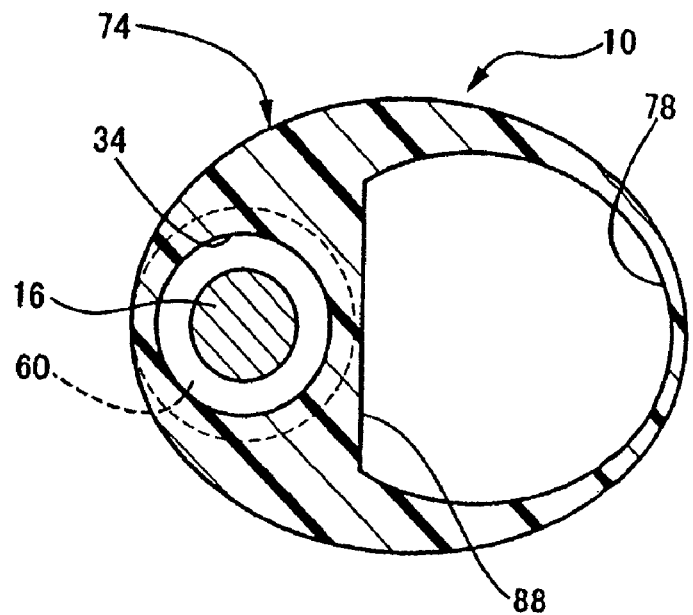
FIG. 20 is an embodiment corresponding to FIG. 17, showing another embodiment of a reagent injection device conforming to the present invention.
Figure 21:
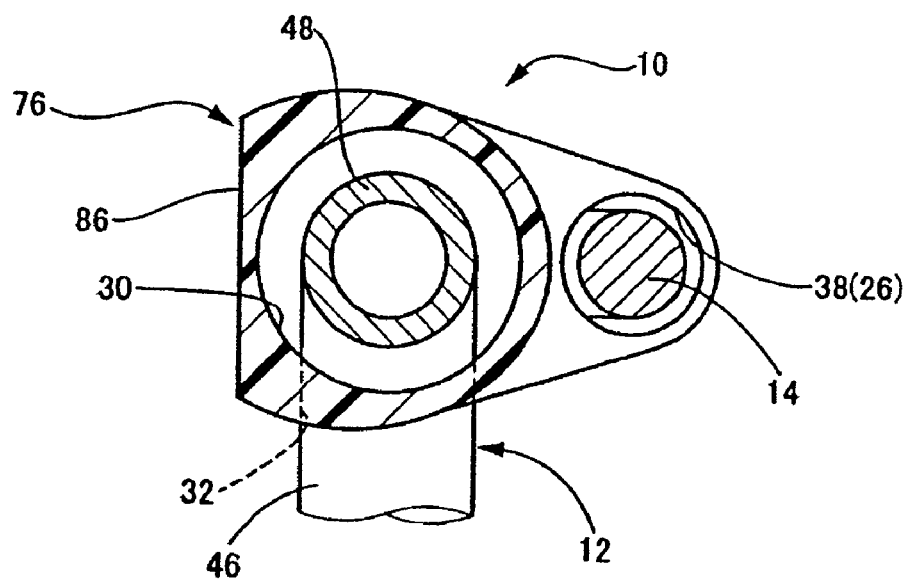
FIG. 21 is a drawing corresponding to FIG. 18, illustrating the reagent injection device shown in FIG. 20.

Furthermore, in the aforementioned third embodiment the inner tube (76) and outer tube (74) can be moved relatively in the circumferential direction. However, it is also possible, for example, to provide engagement surfaces (86 and 88), which are flat surfaces extending in the radial direction and contact and engage with each other in the circumferential direction, in the corresponding locations of the outer periphery surface of the inner tube (76) and the inner periphery of the outer tube (74), as shown in FIGS. 20 and 21. This way, relative movement of the inner tube (76) and outer tube (74) in the circumferential direction can be prevented. This, in turn, favorably prevents unnecessary movements of the support tube (60) in the circumferential direction due to relative movements of the inner tube and outer tube in the circumferential direction. As a result, insertion of the main tube (10) into the main vessel (66), and consequently insertion of a reagent, can be performed in a more stable and smoother manner.

Of course, it is also possible to attach an inflatable/deflatable balloon of a known structure externally to the main tube (10). This way, the positional stability of the main tube (10) in the main vessel (66) can be favorably enhanced. As a result, the needle piercing operation, and consequently the reagent injection operation, can be performed in a more stable and easier manner. If a balloon is attached externally to the main tube (10), the main tube (10) must have a channel (balloon lumen) through which to pass a liquid, such as saline solution, for inflating the balloon.

Additionally, the aforementioned first embodiment adopted a structure in which one end of the first guide wire (14) is extended out of the third opening (38) provided in the middle of the main tube (10) (this structure is called "rapid-exchange type" or "monorail type"), as well as a structure in which the second guide wire (16) is inserted from the proximal end of the main tube (10) (this structure is called "over-the-wire type"). However, instead of these structures it is also possible, for example, to adopt the over-the-wire type or rapid-exchange type for both the first guide wire (14) and second guide wire (16). Similarly, the over-the-wire type can be used for the first guide wire (14) and the rapid-exchange type for the second guide wire (16).

The aforementioned embodiments provided specific applications of the present invention as reagent injection catheters used for injecting reagents into lesions in the cardiac muscle. However, of course the present invention can also be applied favorably as reagent injection catheters used for injecting reagents into various body tissues in different organs other than the cardiac muscle, including the bone marrow, or as other reagent injection devices not categorized as "catheter" that can be used for injecting reagents into lesions in the cardiac muscle or tissues in other areas of the human body.

Although a complete list is not provided, the present invention can be implemented in a variety of modes that reflect various changes, modifications, improvements, etc., based on the knowledge of those skilled in the art. It goes without saying that these modes are also included in the scope of the present invention unless they clearly deviate from the purpose of the present invention.

The present application claims priority to Japanese Patent Application No. 2004-304822, filed Oct. 19, 2004, the disclosure of which is incorporated herein by reference in its entirety.

INDUSTRIAL APPLICABILITY

Using the reagent injection devices of the present invention, therapies and Other procedures in which a specified reagent is injected into a lesion in body tissue can be carried out. The injection device can be made thinner or smaller and is able to reliably puncture a specified position in the target body tissue with the needle. The injection device allows a user to accurately grasp the inserted depth of the needle when the target body tissue is punctured with the needle in a reliable manner.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An injection device comprising:
   an inner tube having a first lumen extending in an axial direction of the inner tube,
   a tubular body movably inserted into said inner tube, said tubular body having a pointed tip and an aperture to permit reagent to flow therethrough,
   the first lumen having a projection aperture allowing said tip of the tubular body to project therethrough to enable injection of a reagent into a patient body, said projection aperture being on a lateral portion of the inner tube, and
   a second lumen extending in the axial direction of the inner tube for a first guide wire movably inserted thereinto; and
   an outer tube having an inner cavity receiving the inner tube relatively movable in the axial direction of the outer tube, the outer tube comprising a support tube branching from the outer tube, having a free tip and an inner hole for supporting a second guide wire, said support tube being formed integrally with a distal portion of the outer tube.

2. The injection device as claimed in claim 1, further comprising an engagement portion where an inner periphery surface of the inner cavity of the outer tube and an outer periphery surface of the inner tube are engaged with each other to inhibit relative movement of the outer tube and the inner tube in a circumferential direction.

3. The injection device as claimed in claim 1, wherein the support tube comprises a base part and a tip part which is more flexible than the base part.

4. The injection device as claimed in claim 1, wherein the outer tube has a third lumen extending in the axial direction of the outer tube for the second guide wire movably inserted therinto and connected with the inner hole of the support tube.

* * * * *